US008974381B1

(12) United States Patent
Lovell et al.

(10) Patent No.: US 8,974,381 B1
(45) Date of Patent: Mar. 10, 2015

(54) CERVICAL RETRACTOR

(75) Inventors: Nathan Lovell, Oceanside, CA (US);
Michael Serra, San Diego, CA (US);
Michael Brotman, San Diego, CA (US);
Andrew Wolf, Del Mar, CA (US);
Richard Lazar, Colorado Springs, CO
(US); Jennifer Simon, Colorado
Springs, legal representative, CO (US);
Kenneth Rich, Raleigh, NC (US);
Sandeep Kunwar, Woodside, CA (US)

(73) Assignee: NuVasive, Inc., San Diego, CA (US)

( * ) Notice: Subject to any disclaimer, the term of this patent is extended or adjusted under 35 U.S.C. 154(b) by 363 days.

(21) Appl. No.: 13/507,111

(22) Filed: Jun. 4, 2012

Related U.S. Application Data

(63) Continuation-in-part of application No. 13/457,484, filed on Apr. 26, 2012.

(60) Provisional application No. 61/479,307, filed on Apr. 26, 2011, provisional application No. 61/493,397, filed on Jun. 3, 2011.

(51) Int. Cl.
*A61B 17/02* (2006.01)

(52) U.S. Cl.
USPC ............ 600/232; 600/215; 600/219; 600/222

(58) Field of Classification Search
CPC ............... A61B 17/0218; A61B 17/02; A61B 17/0206; A61B 17/0293
USPC .................................................. 606/201–246
See application file for complete search history.

(56) References Cited

U.S. PATENT DOCUMENTS

| 186,637 A | 1/1877 | Tanner |
| 1,223,812 A | 4/1917 | Listiak |
| 1,456,116 A | 5/1923 | Bessesen |
| 2,807,259 A | 9/1957 | Guerriero |
| 3,030,948 A | 4/1962 | Loeffler |
| 3,384,077 A | 5/1968 | Gauthier |
| 3,509,873 A | 5/1970 | Karlin |
| 3,522,799 A | 8/1970 | Gauthier |
| 3,724,449 A | 4/1973 | Gauthier |
| 3,749,088 A | 7/1973 | Kohlmann |
| 3,965,890 A | 6/1976 | Gauthier |
| 4,024,859 A | 5/1977 | Slepyan |
| 4,116,232 A | 9/1978 | Rabban |
| 4,151,837 A | 5/1979 | Millard |
| 4,156,424 A | 5/1979 | Burgin |

(Continued)

FOREIGN PATENT DOCUMENTS

| CA | 1142826 | 3/1983 |
| CN | 201341901 | 11/2009 |

(Continued)

*Primary Examiner* — Jerry Cumberledge
(74) *Attorney, Agent, or Firm* — Jonathan Spangler; Rory Schermerhorn

(57) ABSTRACT

An anterior cervical retractor comprises a first medial-lateral retractor body having a base arm and a moving arm and a pair of retractor blades. The retractor blades may be side loading or top loading. The cervical retractor comprises a second cranial-caudal retractor body having a pair of moving arms and a pair of retractor blades. The retractor blades may have an adjustable angulation. The retractor blades may also be fixed to the spine and provide distraction upon operation of the second retractor body. The blades of the first retractor body and/or the second retractor body may be coupled to light elements that illuminate the operative corridor between the blades.

19 Claims, 22 Drawing Sheets

(56) References Cited

U.S. PATENT DOCUMENTS

| | | | |
|---|---|---|---|
| 4,165,746 A | 8/1979 | Burgin | |
| 4,457,300 A | 7/1984 | Budde | |
| 4,461,284 A | 7/1984 | Fackler | |
| 4,686,972 A | 8/1987 | Kurland | |
| 4,702,230 A | 10/1987 | Pelta | |
| 4,747,394 A | 5/1988 | Watanabe | |
| 4,747,395 A | 5/1988 | Brief | |
| 4,817,587 A | 4/1989 | Janese | |
| 4,829,985 A | 5/1989 | Couetil | |
| 4,852,552 A | 8/1989 | Chaux | |
| 4,881,525 A | 11/1989 | Williams | |
| 4,934,352 A | 6/1990 | Sullivan | |
| 5,052,373 A | 10/1991 | Michelson | |
| 5,512,038 A | 4/1996 | O'Neal | |
| D369,860 S | 5/1996 | Koros | |
| 5,733,290 A | 3/1998 | McCue | |
| 5,772,583 A | 6/1998 | Wright | |
| 5,795,291 A * | 8/1998 | Koros et al. | 600/232 |
| 5,846,192 A | 12/1998 | Teixido | |
| 5,865,730 A | 2/1999 | Fox | |
| 5,882,298 A | 3/1999 | Sharratt | |
| 5,893,831 A | 4/1999 | Koros | |
| 5,902,233 A | 5/1999 | Farley | |
| 5,931,777 A | 8/1999 | Sava | |
| 5,944,658 A * | 8/1999 | Koros et al. | 600/232 |
| 5,967,974 A | 10/1999 | Nicholas | |
| 5,984,865 A * | 11/1999 | Farley et al. | 600/213 |
| 5,993,385 A | 11/1999 | Johnston | |
| 6,042,540 A | 3/2000 | Johnston | |
| 6,042,542 A * | 3/2000 | Koros et al. | 600/231 |
| 6,200,263 B1 | 3/2001 | Person | |
| 6,206,826 B1 | 3/2001 | Mathews | |
| 6,206,828 B1 * | 3/2001 | Wright | 600/232 |
| 6,213,941 B1 | 4/2001 | Benetti | |
| 6,224,545 B1 | 5/2001 | Cocchia | |
| 6,234,961 B1 | 5/2001 | Gray | |
| 6,241,729 B1 | 6/2001 | Estes | |
| 6,264,396 B1 | 7/2001 | Dobrovolny | |
| 6,296,609 B1 | 10/2001 | Brau | |
| 6,322,500 B1 | 11/2001 | Sikora | |
| 6,340,345 B1 | 1/2002 | Lees | |
| 6,416,465 B2 | 7/2002 | Brau | |
| 6,506,151 B2 | 1/2003 | Estes | |
| 6,524,238 B2 | 2/2003 | Velikaris | |
| 6,602,190 B2 | 8/2003 | Dobrovolny | |
| 6,648,818 B2 | 11/2003 | Cartier | |
| 6,685,632 B1 | 2/2004 | Hu | |
| 6,692,434 B2 | 2/2004 | Ritland | |
| 6,733,444 B2 | 5/2004 | Phillips | |
| 6,860,850 B2 | 3/2005 | Phillips | |
| 6,887,197 B2 | 5/2005 | Phillips | |
| 6,887,198 B2 | 5/2005 | Phillips | |
| 6,929,606 B2 | 8/2005 | Ritland | |
| 6,951,538 B2 | 10/2005 | Ritland | |
| 7,001,333 B2 | 2/2006 | Hamel | |
| 7,014,609 B2 | 3/2006 | Cartier | |
| 7,056,287 B2 | 6/2006 | Taylor | |
| 7,108,698 B2 | 9/2006 | Robbins | |
| 7,147,599 B2 | 12/2006 | Phillips | |
| 7,150,714 B2 * | 12/2006 | Myles | 600/205 |
| 7,166,073 B2 | 1/2007 | Ritland | |
| 7,182,729 B2 | 2/2007 | Abdelgany | |
| 7,182,731 B2 | 2/2007 | Nguyen | |
| 7,214,186 B2 | 5/2007 | Ritland | |
| 7,235,048 B2 | 6/2007 | Rein | |
| 7,294,104 B2 | 11/2007 | Person | |
| 7,374,534 B2 | 5/2008 | Dalton | |
| 7,396,328 B2 | 7/2008 | Penenberg | |
| 7,455,639 B2 | 11/2008 | Ritland | |
| 7,473,223 B2 | 1/2009 | Fetzer | |
| 7,537,565 B2 | 5/2009 | Bass | |
| 7,569,014 B2 | 8/2009 | Bass | |
| 7,588,537 B2 | 9/2009 | Bass | |
| 7,654,954 B1 | 2/2010 | Phillips | |
| 7,722,618 B2 | 5/2010 | Estes | |
| 7,744,530 B2 | 6/2010 | Person | |
| 7,753,844 B2 | 7/2010 | Sharratt | |
| 7,758,501 B2 | 7/2010 | Frasier | |
| 7,850,608 B2 | 12/2010 | Hamada | |
| 7,909,829 B2 | 3/2011 | Patel | |
| 7,909,848 B2 | 3/2011 | Patel | |
| 7,927,337 B2 | 4/2011 | Keller | |
| 7,931,589 B2 | 4/2011 | Cohen | |
| 7,935,053 B2 | 5/2011 | Karpowicz | |
| 7,946,982 B2 | 5/2011 | Hamada | |
| 7,959,564 B2 | 6/2011 | Ritland | |
| 7,981,031 B2 | 7/2011 | Frasier | |
| 8,062,217 B2 | 11/2011 | Boucher | |
| 8,066,710 B2 | 11/2011 | Estes | |
| 8,617,063 B2 * | 12/2013 | Loftus et al. | 600/227 |
| 8,636,655 B1 | 1/2014 | Childs | |
| 8,663,100 B2 * | 3/2014 | Miles et al. | 600/202 |
| 2005/0192486 A1 | 9/2005 | Hamel | |
| 2005/0240081 A1 | 10/2005 | Eliachar | |
| 2006/0183978 A1 | 8/2006 | Howard | |
| 2006/0206009 A1 | 9/2006 | Von Wald | |
| 2007/0038033 A1 | 2/2007 | Jones | |
| 2007/0073112 A1 | 3/2007 | Holmes | |
| 2007/0083086 A1 | 4/2007 | LeVahn | |
| 2007/0100212 A1 * | 5/2007 | Pimenta et al. | 600/210 |
| 2007/0129608 A1 | 6/2007 | Sandhu | |
| 2007/0208228 A1 | 9/2007 | Pavento | |
| 2007/0238932 A1 | 10/2007 | Jones | |
| 2008/0071145 A1 | 3/2008 | Bjork | |
| 2008/0114208 A1 | 5/2008 | Hutton | |
| 2008/0146881 A1 | 6/2008 | Alimi | |
| 2008/0249272 A1 | 10/2008 | Reglos | |
| 2009/0012370 A1 | 1/2009 | Gutierrez | |
| 2009/0012527 A1 | 1/2009 | Mignucci | |
| 2009/0076333 A1 | 3/2009 | Bjork | |
| 2009/0076516 A1 | 3/2009 | Lowry | |
| 2009/0105547 A1 | 4/2009 | Vayser | |
| 2009/0124861 A1 | 5/2009 | Fetzer | |
| 2009/0227845 A1 | 9/2009 | Lo | |
| 2010/0081885 A1 * | 4/2010 | Wing et al. | 600/215 |
| 2010/0113885 A1 | 5/2010 | Mcbride | |
| 2010/0217089 A1 | 8/2010 | Farley | |
| 2010/0298647 A1 | 11/2010 | Black | |
| 2010/0298648 A1 | 11/2010 | Gray | |
| 2010/0312068 A1 | 12/2010 | Dalton | |
| 2011/0004067 A1 | 1/2011 | Marchek | |
| 2011/0034781 A1 | 2/2011 | Loftus | |
| 2011/0130793 A1 | 6/2011 | Woolley | |
| 2011/0137130 A1 | 6/2011 | Thalgott | |
| 2011/0144450 A1 | 6/2011 | Paolitto | |
| 2011/0172494 A1 | 7/2011 | Bass | |
| 2011/0201897 A1 | 8/2011 | Bertagnoli | |
| 2011/0208008 A1 | 8/2011 | Michaeli | |
| 2011/0224497 A1 | 9/2011 | Weiman | |
| 2011/0245836 A1 | 10/2011 | Hamada | |
| 2011/0257487 A1 | 10/2011 | Thalgott | |
| 2011/0301423 A1 | 12/2011 | Koros | |
| 2012/0083662 A1 | 4/2012 | Hamada | |
| 2012/0130180 A1 | 5/2012 | Pell | |
| 2012/0172670 A1 | 7/2012 | Hamada | |
| 2012/0197300 A1 | 8/2012 | Loftus | |
| 2012/0245432 A1 | 9/2012 | Karpowicz | |
| 2012/0265021 A1 | 10/2012 | Nottmeier | |
| 2012/0330106 A1 * | 12/2012 | Wright et al. | 600/218 |
| 2013/0046147 A1 | 2/2013 | Nichter | |
| 2013/0123581 A1 | 5/2013 | Fritzinger | |
| 2013/0158359 A1 | 6/2013 | Predick | |
| 2013/0245383 A1 | 9/2013 | Friedrich | |
| 2013/0261401 A1 | 10/2013 | Hawkins | |
| 2013/0261402 A1 | 10/2013 | Hawkins | |
| 2013/0303859 A1 | 11/2013 | Nowak | |
| 2013/0345520 A1 | 12/2013 | Hamada | |
| 2014/0024900 A1 | 1/2014 | Capote | |
| 2014/0066718 A1 | 3/2014 | Fiechter | |
| 2014/0066941 A1 | 3/2014 | Mignucci | |

(56) References Cited

U.S. PATENT DOCUMENTS

FOREIGN PATENT DOCUMENTS

| | | |
|---|---|---|
| CN | 201537102 | 8/2010 |
| DE | 29722605 | 2/1998 |
| EP | 1949860 | 3/2010 |
| EP | 2394584 | 12/2011 |
| FR | 2788958 | 8/2000 |
| GB | 1520832 | 8/1978 |
| JP | 10277043 | 10/1998 |
| WO | WO2004037070 | 5/2004 |
| WO | WO-2004047650 | 6/2004 |
| WO | WO2007002405 | 1/2007 |
| WO | WO2010057980 | 5/2010 |
| WO | WO2012005914 | 1/2012 |
| WO | WO2012040206 | 3/2012 |
| WO | WO2012093368 | 7/2012 |
| WO | WO2012125975 | 9/2012 |
| WO | WO2013000105 | 1/2013 |
| WO | WO2013033630 | 3/2013 |
| WO | WO2013052827 | 4/2013 |

* cited by examiner

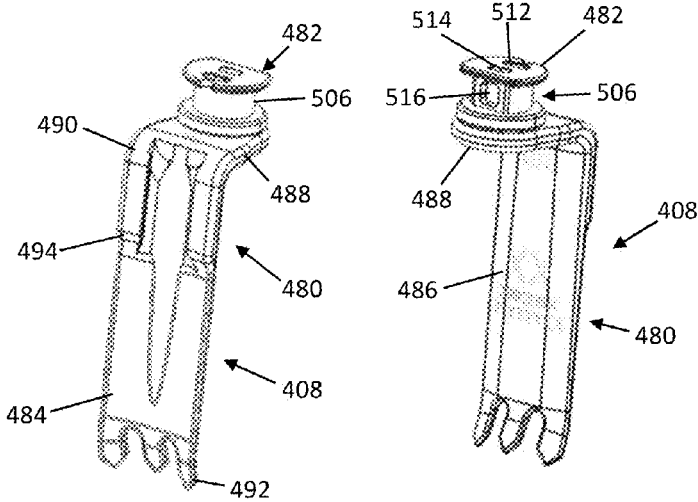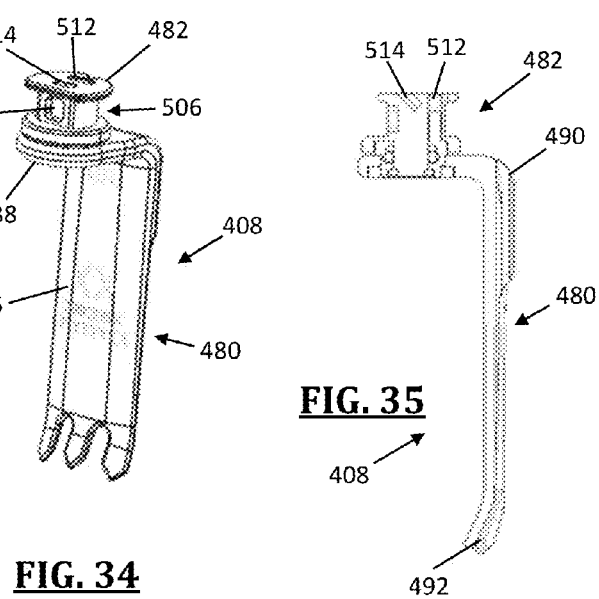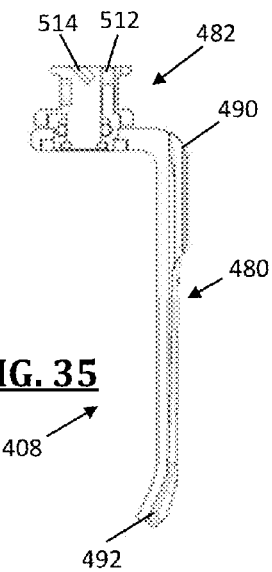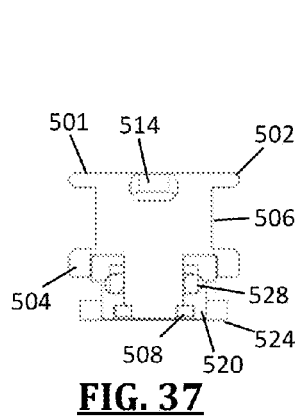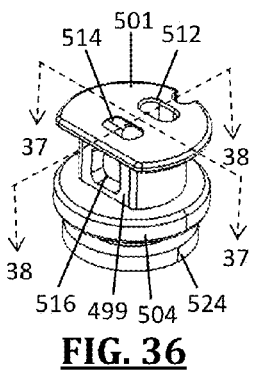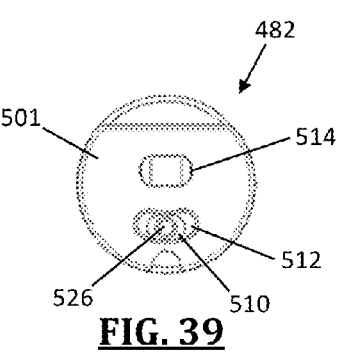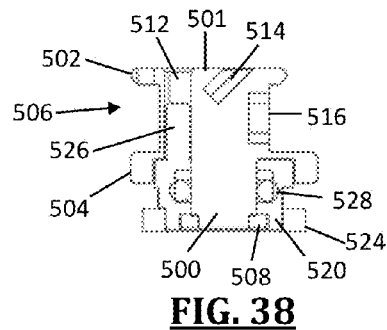

US 8,974,381 B1

CERVICAL RETRACTOR

CROSS REFERENCES TO RELATED APPLICATIONS

This application is a continuation-in-part of the U.S. patent application Ser. No. 13/457,484, filed Apr. 26, 2012, which claims the benefit of priority from U.S. Provisional Patent Application Ser. No. 61/479,307 filed on Apr. 26, 2011, the entire contents of which are each hereby expressly incorporated by reference into this disclosure as if set forth in its entirety herein. This application also claims the benefit of priority from U.S. Provisional Patent Application Ser. No. 61/493,397 filed on Jun. 3, 2011, the entire contents of which are each hereby expressly incorporated by reference into this disclosure as if set forth in its entirety herein.

TECHNICAL FIELD

This application describes surgical retractors useful for creating and maintaining an access corridor to the cervical spine.

BACKGROUND

Retractors are often used to assist surgeons during procedures. During spinal procedures for example, retractors are used to maintain an operative corridor free of body tissue from the exterior of the patient to the spinal target site. Procedures performed on the anterior cervical spine, for example, discectomy, fusion, disc replacement, etc . . . are often performed with the aid of the retractor. These procedures are used to treat symptoms from cervical disc diseases or traumas such as cervical radiculopathy, disc herniations, fractures, and spinal instability.

In order to perform the anterior cervical discectomy, an incision is made through the neck and retractors are then used to gently separate and hold the neck muscles and soft tissues apart so that the surgeon can work on the front portion of the cervical spine. While there are a number of cervical retractors available for use, there remains room for improvement of cervical retractor offerings. For example, cervical retractors often use retractor blades that are fixed in a single position. These retractor blades are unable to adjust or move with the tissue as the tissue is retracted and pressure points can arise potentially causing unnecessary morbidity to the surrounding tissue. Other retractors used blades that are free to rotate relative to the retractor body. However, because these blades can rotate freely correctly aligning them during retractor deployment can also be a challenge. Additionally, retractors often have many parts that are free to move relative, which may be beneficial to achieve a desired retractor position, but which can lead to difficulty in handling the retractors outside of body.

The retractor, instruments, and methods described herein are aimed at addressing these and other challenges that currently exist.

BRIEF DESCRIPTION OF THE DRAWINGS

Elements in the figures have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention, thus the drawings are generalized in form in the interest of clarity and conciseness.

FIGS. 33-34 are front perspective and back perspective views of a side loading retractor blade of the retractor system of FIG. 29, according to one example embodiment;

FIG. 35 is a side cross-section view of the retractor blade of FIGS. 33-34;

FIG. 36 is a perspective view of a connection post of the retractor blade of FIGS. 33-35;

FIG. 37 is a cross-section view of the connection post of FIG. 36;

FIG. 38 is another cross section view of the connection post of FIG. 36;

FIG. 39 is a top view of the connection post of FIG. 36;

DETAILED DESCRIPTION OF EXAMPLE EMBODIMENTS

Illustrative embodiments are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The anterior cervical retractor disclosed herein boasts a variety of inventive features and components that warrant patent protection, both individually and in combination.

Figure 1:
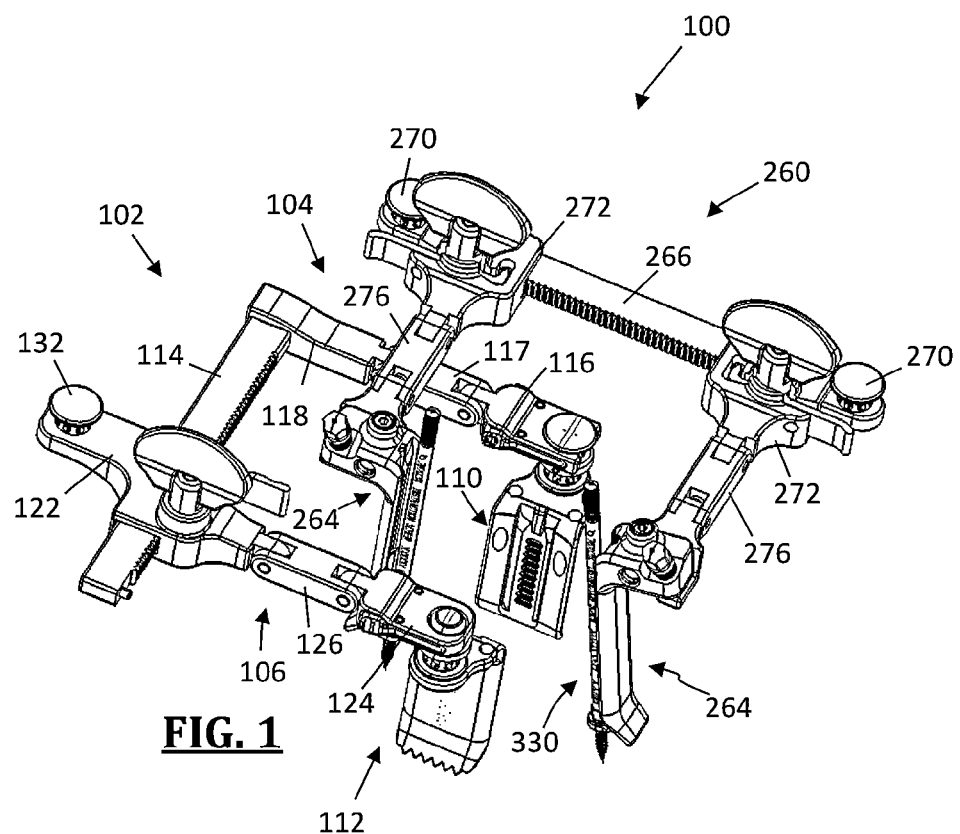
FIG. 1 is a perspective view of an anterior cervical retractor system according to one example embodiment.

FIG. 1 is a perspective view of a cervical retractor system 100 according to one example embodiment. The cervical retractor system 100 includes a first retractor 102 and a second retractor 260. According to a preferred example, the first retractor 102 is a medial-lateral retractor (i.e. tissue is retracted in the medial and lateral directions) and the second retractor 260 is a cranial-caudal retractor (i.e. tissue is retracted in the cranial and caudal directions). At the outset it is noted that while the first retractor 102 and second retractor 260 are designed to be used together, either of the first retractor 102 and the second retractor 260 may be utilized alone. By way of example, the use of the second retractor 260 may not be necessary for single level exposure. Instead, the second retractor 260 is particularly useful during multi-level procedures to prevent tissue creep into the larger exposures. The second retractor 260 can also be used to distract the disc space between the vertebrae during single level or multi-level cases.

Figure 2:
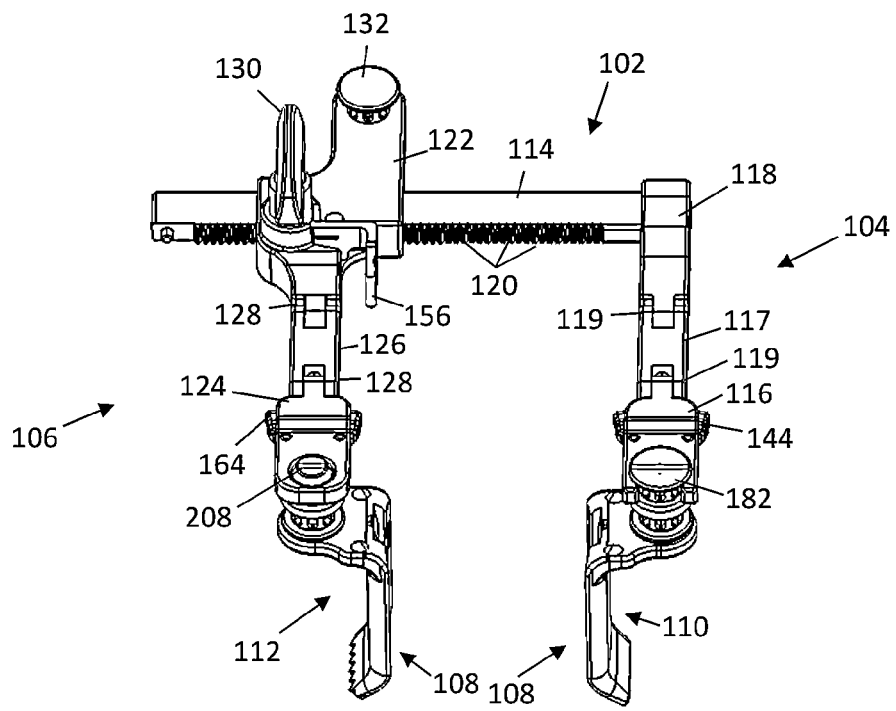
FIG. 2 is a perspective view of one example of a first, medial-lateral retractor of the retractor system of FIG. 1.

With reference to FIG. 2, the first retractor 102 according to one example embodiment is depicted. The first retractor 102 includes a base arm 104 and a moving arm 106 and, a pair of retractor blades 108 having a side loading blade 110 and a top loading blade 112. The base arm 104 includes a track base 118 and a side loading connector 116 that connects the side loading blade 110. The side loading connector 116 is connected to the track base 118 by a pivot link 117 having two pivots 119 such that the base arm comprises a double hinge. A first track 114 extends perpendicularly from the track base 118 of the base arm 104, the first track 114 including a row of teeth 120. The moving arm 106 is located opposite to the base arm 104. The moving arm 106 includes a first track receptacle 122 and a top loading connector 124 that connects the top loading blade 112. The top loading connector 124 is connected to the track receptacle 122 by a pivot link 126 having two pivots 128 such that the moving arm comprises a double hinge. The moving arm 106 may be advanced along the first track 114 by means of a knob 130 to move the moving arm 106 away from the base arm 104. The moving arm 106 also includes an articulating arm post 132 which provides a connection point for rigidly attaching the first retractor 102 to the surgical table (or other stationary object) with a locking articulating arm.

In surgical use, according to a preferred example, the base arm 104 and the side loading connector 116 are positioned medially (away from the surgeon) and against the esophagus and trachea. The moving arm 106 and the top loading connector 124 is positioned laterally (closest to the surgeon). Hence, the side loading blade 110 and the top loading blade 112 may also be referred to as medial blade and lateral blade, respectively. The retractor 102 may be then used to retract the tissue in a medial-lateral orientation.

Figure 3:
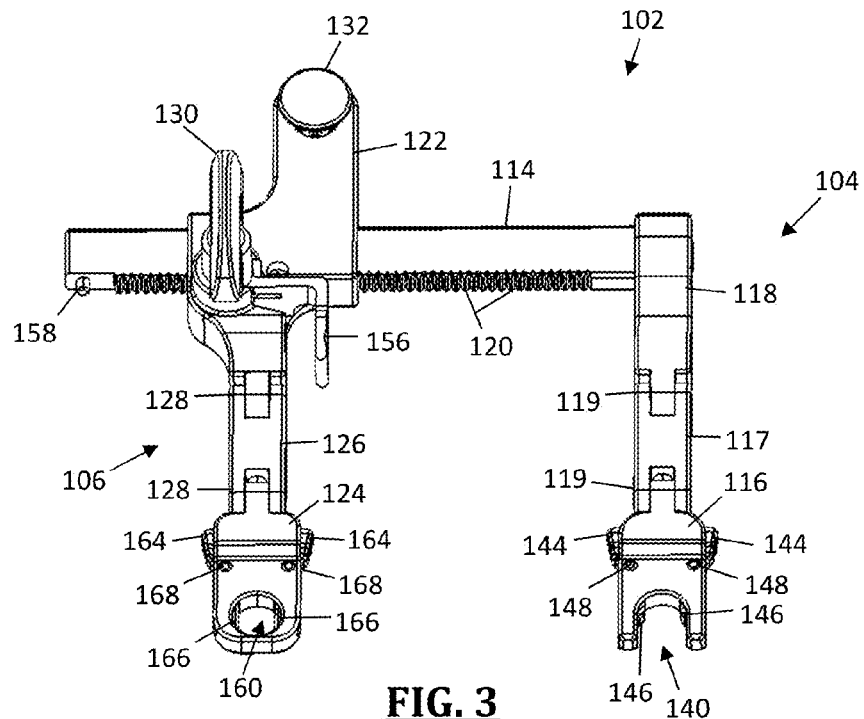
FIG. 3 is a perspective view of the retractor of FIG. 2 without the retractor blades engaged.
Figure 4:
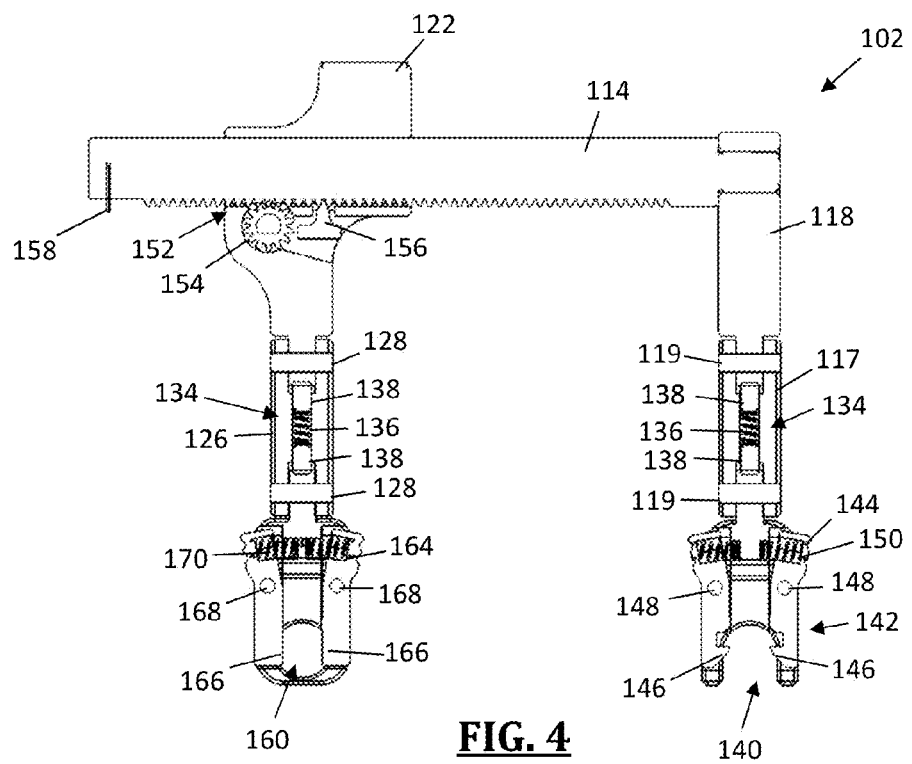
FIG. 4 is a cross section view of the retractor of FIG. 2.

The base arm 104 and moving arm 106 are best illustrated in FIGS. 3-4. The side loading connector 116 is connected to the track base 118 by pivot link 117. The pivot link 117 includes a pair of pivots 119 with one pivot 119 located on each end of the pivot link 117 to permit variability in the height of the side loading connector 116 relative to the track base 118 while maintaining the alignment of the side loading connector 116 generally parallel to the track base 118. The pivot link 117 further includes a friction mechanism 134 for preventing the side loading connector 116 and the pivot link 117 from flopping around. The friction mechanism 134 includes a spring 136 with a pair of friction nubs 138 situated at each end. The friction mechanism 134 creates friction between the first pivot link 117 and the side loading connector 116, and between the pivot link 117 and the track base 118. The friction between the pivot link 117 and each of the side loading connector 116 and the track base 118 is such that the application of force (e.g. directly from the user or from contact with the patient or another retractor, etc . . . ) is required to adjust the position of the side loading connector 116. This way the side loading connector 116 and pivot link 117 will not flop around and create a disturbance when handling the retractor 102 and particularly when trying to position the retractor 102 in the patient.

The side loading connector 116 includes an open receptacle 140 opening in the free end of the connector 116. Situated along each side of the side loading connector 116 are locking arms 142 that each include a release tab 144 at one end and a locking tooth 146 at the opposite end, the release tab 144 and locking tooth 146 being separated by a pivot 148 that pivotally connects the locking arms 142 to the connector 116. Each of the locking arms 142 is spring loaded with a spring 150 that biases the locking tooth 146 into the open receptacle 140 where it engages with connection post of the side loading retractor blade 110 to lock the blade 110 to the connector. To disengage the side loading blade from the side loading connector 116, the release tabs 144 are depressed which causes the teeth 146 to withdraw into the connector clearing the way for removal of the connection post from the open receptacle 140. A tapered front edge on tooth 146 permits loading of the blade without depressing the release tab 144 to clear the tooth out of the open receptacle 140.

The top loading connector 124 is connected to the track receptacle 122 by pivot link 126. The pivot link 126 includes a pair of pivots 128 with one pivot 128 located on each end of the pivot link 126 to permit variability in the height of the top loading connector 124 relative to the track receptacle 122 while maintaining the alignment of the top loading connector 124 generally parallel to the track receptacle 122. The pivot link 126 further includes a friction mechanism 134 for preventing the top loading connector 124 and the pivot link 126 from flopping around. The friction mechanism 134 includes a spring 136 with a pair of friction nubs 138 situated at each end. The friction mechanism 134 creates friction between the first pivot link 126 and the top loading connector 124, and between the pivot link 126 and the track receptacle 122. The friction between the pivot link 126 and each of the top loading connector 124 and the track receptacle 122 is such that the application of force (e.g. directly from the user or from contact with the patient or another retractor, etc . . . ) is required to adjust the position of the top loading connector 124. This way the top loading connector 124 and pivot link 126 will not flop around and create a disturbance when handling the retractor 102 and particularly when trying to position the retractor 102 in the patient.

The track receptacle 122 has a passage 152 through which the track 114 passes and which permits the moving arm 106 to translate along the track 114. The moving arm 106 is advanced towards or away from the base arm 104 by turning the knob 130. A gear 154 on the knob 130 extends into track receptacle passage 152 and engages the teeth 120 such that rotation of the knob 130 translates the moving arm 106 along the track either towards or away from the base arm 104, depending on the direction of rotation. The movement of the moving arm 106 towards the base arm 104 is prevented by a lock 156 that engages the track teeth 120 in such a way that motion away from the base arm 106 is permitted while motion towards the base arm is inhibited. By way of example, the lock 156 may be a spring biased pawl pivotally coupled to the track receptacle. The knob 130 may preferably include a friction mechanism to prevent the knob 130 from flopping around. For example, the friction mechanism (not shown) may be similar to the friction mechanism 134 that includes a spring biased friction nub in contact with a hinged portion of the knob. A protrusion 158 on the end of the track 114 prohibits the track receptacle 122 from disengaging from the track 114.

The top loading connector 124 includes a closed receptacle 160 enclosed by the connector 124. Situated along each side of the top loading connector 124 are locking arms 162 that each include a release tab 164 at one end and a locking wedge 166 at the opposite end, the release tab 164 and locking wedge 166 being separated by a pivot 168 that pivotally connects the locking arms 162 to the connector 124. Each of the locking arms 162 is spring loaded with a spring 168 that biases the locking wedge 166 into the closed receptacle 160 where it engages with connection post of the top loading retractor blade 112 to lock the blade 112 to the connector 124. To disengage the top loading blade from the top loading connector 124, the release tabs 164 are depressed which causes the wedges 166 to withdraw into the connector, clearing the way for removal of the connection post from the closed receptacle 160. An upward tapering bottom surface of the locking wedges 166 permit loading of the blade without depressing the release tab 166 to clear the locking wedges from the closed receptacle 160.

Figure 5:
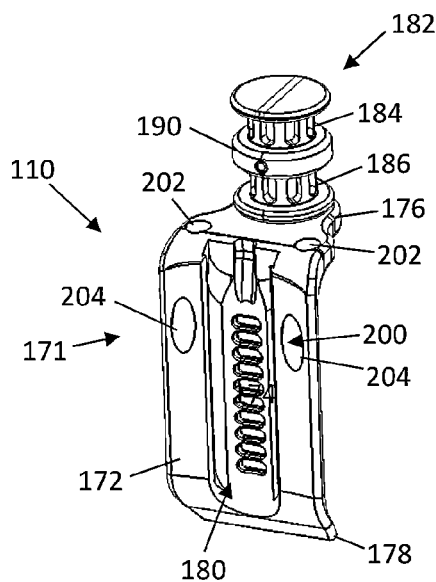
FIGS. 5-7 are front perspective, back perspective, and side exploded views of a side loading retractor blade, according to one example embodiment.
Figure 6:
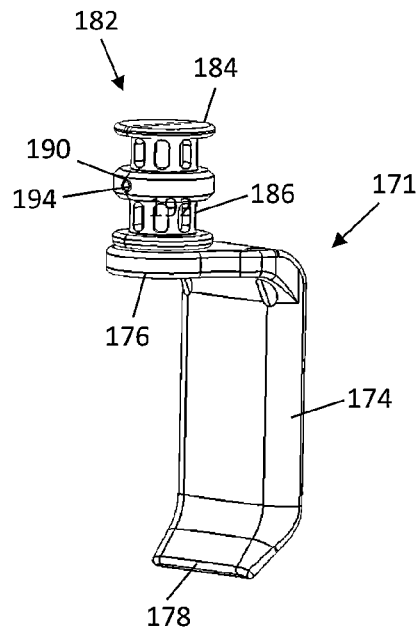
Figure 7:
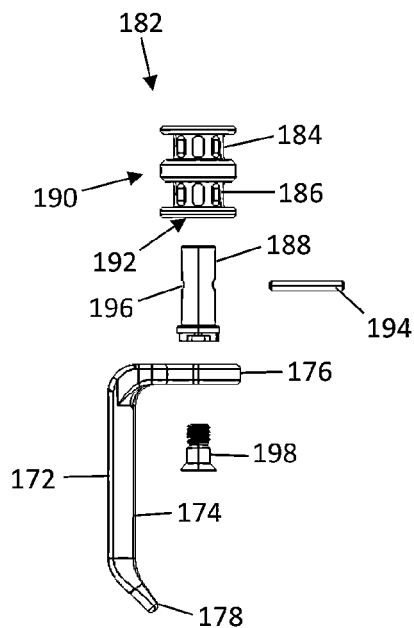

FIGS. 5-7 depict the side loading blade 110. The side loading blade 110 includes a blade portion 171 and a connection post 182. The blade portion 171 includes an interior face 172 that faces the operative corridor, an exterior face 174 that faces and engages the body tissue adjacent the operative corridor, a ledge 176 that extends transversely away from the exterior face 174 at a proximal end 177 of the blade portion, and a distal end 178. The interior face 172 includes a shim track 180 that slidably couple a shim and or lighting elements (not shown). The side loading blade 110 may also include at least one suction channel 200 having a suction receptacle 202 and a suction outlet 204. The at least one suction channel 200 is designed to receive and hold a suction instrument within the operative corridor. The distal end 178 may have any number of suitable configurations, including blunt or toothed. The distal end 178 may also be angled away from the interior.

The connection post 182 is coupled to the ledge 176 and serves as an attachment structure for coupling the side loading blade 110 to the side loading connector 116. The connection post 180 includes an upper tier 184, a lower tier 186, an inner post 188, an outer post 190 and a friction element 192. The connection post 182 is designed to provide limited rotation relative to the blade portion 171 such that the side loading blade 110 is configured to self align during retraction to reduce pressure points on retracted tissue. The inner post 188 and the outer post 190 of the connection post 182 are connected by an attachment pin 194. The inner post 188 further includes a slot 196 to allow the attachment pin 194 to pass through. The slot 196 receives the attachment pin 194 and allows the outer post 190 and the attachment pin 194 to rotate. The width of the slot 196 is made larger than the width of the attachment pin 194 so as to allow the attachment pin 194 to move freely in the slot 196. The friction element 162 helps to control rotation of the inner post 188 within the outer post 190. The friction element 192 may be an O-ring. The inner post 188 is fixed to the blade portion 171 with a first connection post set screw 198. Having both the upper tier 184 and the lower tier 186 allows the side loading blade 110 to be connected to two instruments simultaneously. For example, the blade may be inserted through a skin incision while connected to a manual insertion handle. Then the connection post 182 may be coupled to the side loading connector 124 prior to removing the manual handle such that retraction is not lost while engaging the blade 110 and connector 124. Alternatively, the blade 110 may be connected directly to an articulating arm (instead of being attached to retractor 102) while it is connected to a manual insertion handle.

Figure 8:
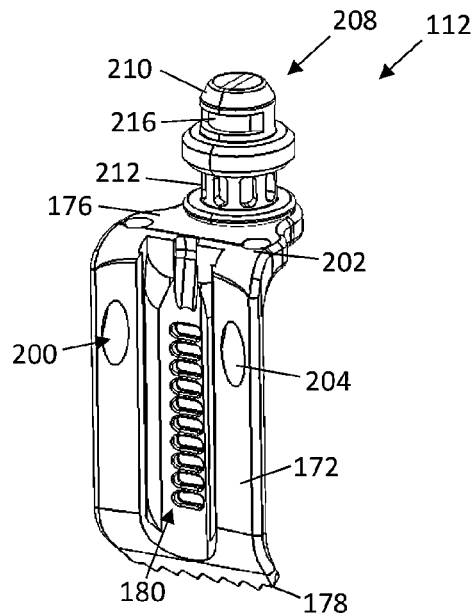
FIGS. 8-10 are front perspective, back perspective, and side exploded views of a top loading retractor blade, according to one example embodiment.
Figure 9:
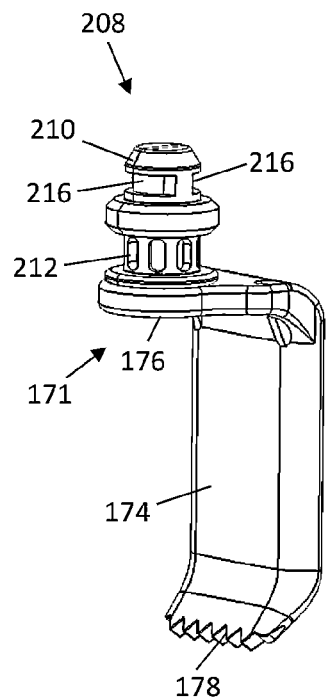
Figure 10:
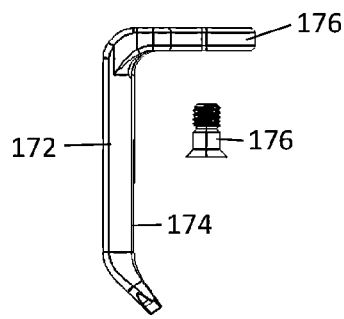

With reference to FIGS. 8-10 the top loading blade 112 is depicted. The top loading blade 112 includes a blade portion 171 and a connection post 208. The blade portion 171 is the same as blade portion 171 of the side loading retractor blade 110. For example, the blade portion includes interior face 172 that faces the operative corridor, an exterior face 174 that faces and engages the body tissue adjacent the operative corridor, a ledge 176 that extends transversely away from the exterior face 174 at a proximal end 177 of the blade portion, and a distal end 178. The interior face 172 includes a shim track 180 that slidably couple a shim and or lighting elements (not shown). The blade portion 171 of top loading blade 112 may also include at least one suction channel 200 having a suction receptacle 202 and a suction outlet 204. The at least one suction channel 200 is designed to receive and hold a suction instrument within the operative corridor. The distal end 178 may have any number of suitable configurations, including blunt or toothed. The distal end 178 may also be angled away from the interior. The top loading blade 112 differs from the side loading blade 110 in the connection post 208 that is connected to the blade portion 171.

The top loading connection post 208 is coupled to the ledge 176 and serves as an attachment structure for coupling the top loading blade 112 to the top loading connector 124. The connection post 208 includes an upper tier 210 and a lower tier 212. The connection post 208 permits rotation of the top loading blade 112 such that the top loading blade 112 self aligns and reduces pressure points on the retracted tissue. Unlike the side loading connector post 182, which rotates (about a limited range) relative to the blade portion 171, the top loading connection post 208 is fixed (via set screw 214) relative to the blade portion 176. Instead, the connection between the upper tier 210 of the connection post 208 and the top loading connector 124 provides for the rotation. Specifically, side grooves 216 formed in the upper tier 210 receive the locking wedges 166. The depth of the side grooves 216 provide for space between the wedges 166 and the inner walls of the grooves 166 which allows rotation (about a limited range) of the top loading blade 112 relative to the top loading connector 124. Having the upper tier 210 and the lower tier 212 allows the top loading blade 112 to be connected to two instruments simultaneously. For example, the blade 112 may be inserted through a skin incision while a manual insertion handle is connected to the lower tier 212. With the manual handle still connected to the lower tier 212, the top loading connector may be attached to the upper tier 210 of the connection post 208 such that retraction is not lost while engaging the blade 110 and connector 124. Alternatively, the blade 112 may be connected directly to an articulating arm (instead of being attached to retractor 102) while it is connected to a manual insertion handle.

Figure 11:
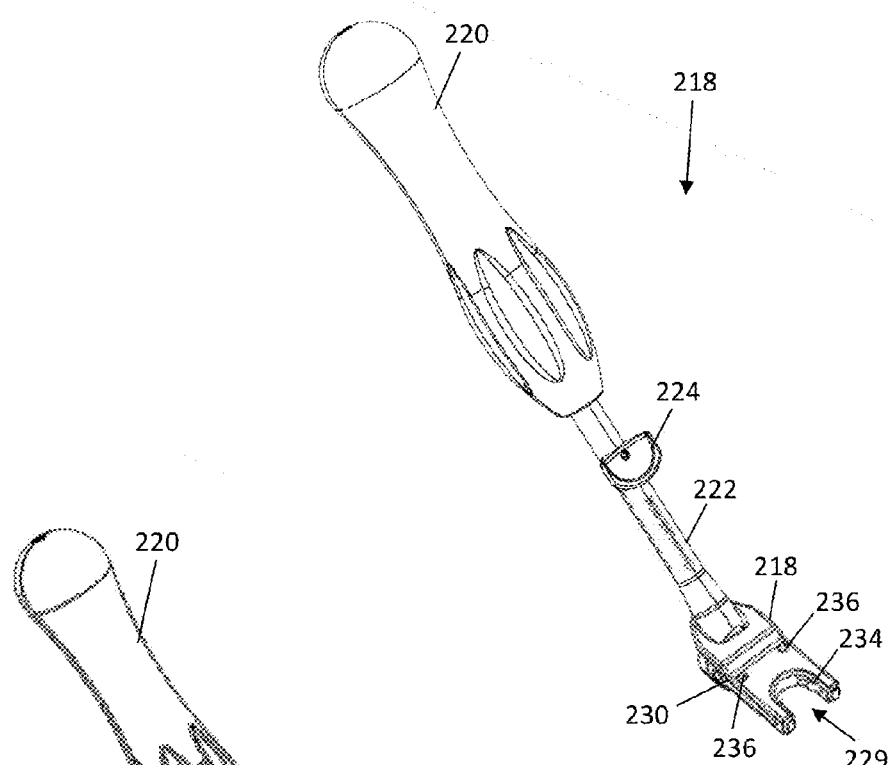
FIG. 11 a perspective view of an insertion handle for use with the side loading retractor blade of FIGS. 5-7 and the top loading retractor blade of FIGS. 8-10, according to one example embodiment.
Figure 12:
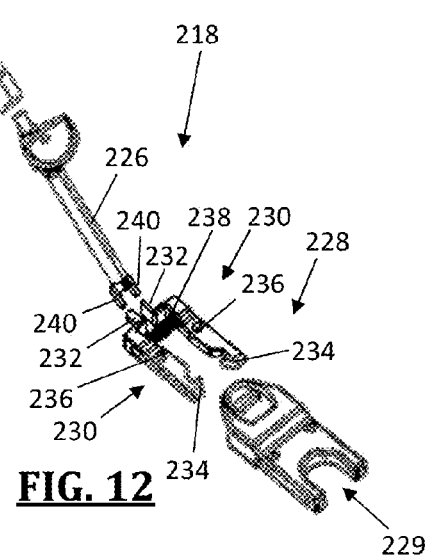
FIG. 12 is an exploded view of the insertion handle of FIG. 11.

FIGS. 11-12 illustrate an insertion handle 218 for advancing the side loading blade 110 and the top loading blade 112 to cervical target site. The insertion handle 218 comprises a grip 220, an outer shaft 222, a lever 224, an inner shaft 226 and an engagement head 228. The engagement head 228 further comprises an open receptacle 229 and a pair of locking arms 230 situated along each side of the side engagement head. Each locking arm 230 includes a tapered engagement extension 232 at one end and a locking tooth 234 at the opposite end, the engagement extension 232 and locking tooth 234 being separated by a pivot 236 that pivotally connects the locking arms 230 to the engagement head 228. The locking arms 230 are spring loaded with a spring 238 that biases the locking teeth 234 into the open receptacle 140 where it engages with either the side loading connection post 182 or the top loading connection post 208. On the side loading blade 110, the insertion handle 218 can connect to either the lower tier 186 or the upper tier 184 of the connection post 182. On the top loading blade 112, the insertion handle 218 can connect to the lower tier 212. A tapered front edge on teeth 234 permit loading of the blade without clearing the teeth 234 out of the open receptacle 229. To withdraw the teeth 234 from the open receptacle and disengage the retractor blade, the lever 22 is depressed. The lever 224 is attached to the inner shaft 226 such that depressing the lever causes the inner shaft 226 to translate towards the engagement head 228. Engagement prongs 240 on the distal end of the inner shaft 226 contact the engagement extensions 232 of the locking arms and force them to move towards each other. The locking arms 230 thus rotate about the pivot 236 and the locking teeth are withdrawn out of the open receptacle 290, freeing the blade 110 or 112.

Figure 13:
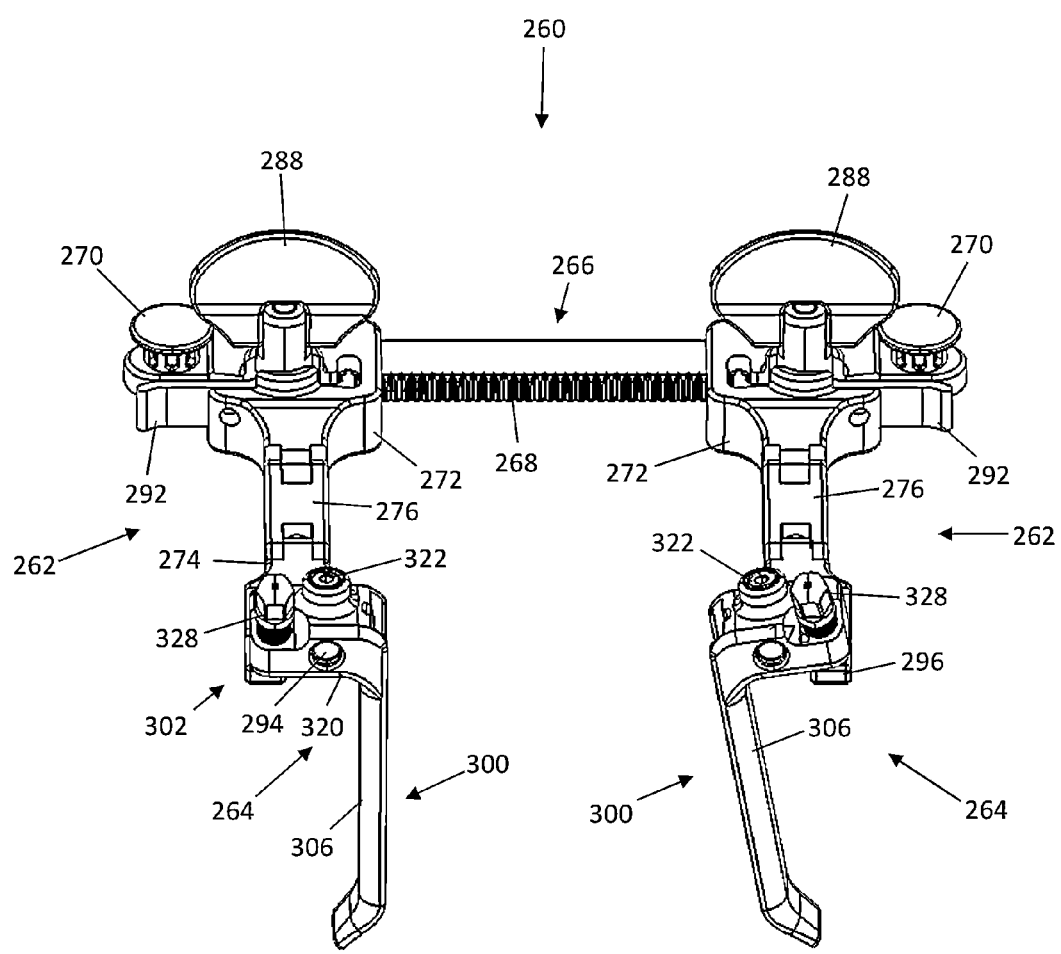
FIG. 13 a perspective view of one example of a second, cranial-caudal retractor of the retractor system of FIG. 1.

With reference to FIG. 13, the second retractor 260 according to one example embodiment is depicted. The second retractor 260 includes a pair of moving arms 262, a pair of blades 264, and a track 266 along which the moving arms 262 translate. In surgical use, according to a preferred example, one moving arm 262 and blade 264 is placed cranially and the other moving arm 262 and blade 264 are placed caudally, thus, the second retractor may also be referred to as the cranial-caudal retractor. As mentioned above, the second retractor may be especially useful to prevent tissue creep during multilevel procedures and during procedures in which distraction of the vertebral bodies is required. The moving arms 262 are identical, but mirror images of each other. Likewise, the blades 264 are identical, but mirror images of each other. Accordingly, the second retractor can be positioned in either of a left (i.e. track is on left) or right (i.e. track is on right) position, depending on the orientation of the first retractor 102 and/or the surgeons preference.

Figure 14:
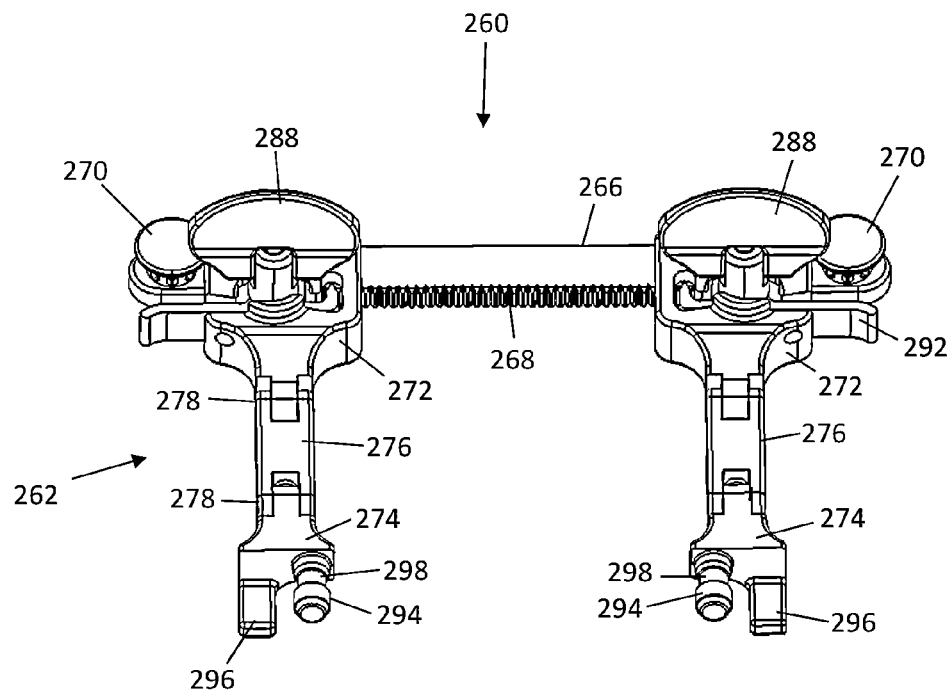
FIG. 14 a perspective view of the retractor of FIG. 13 without the retractor blades engaged.
Figure 15:
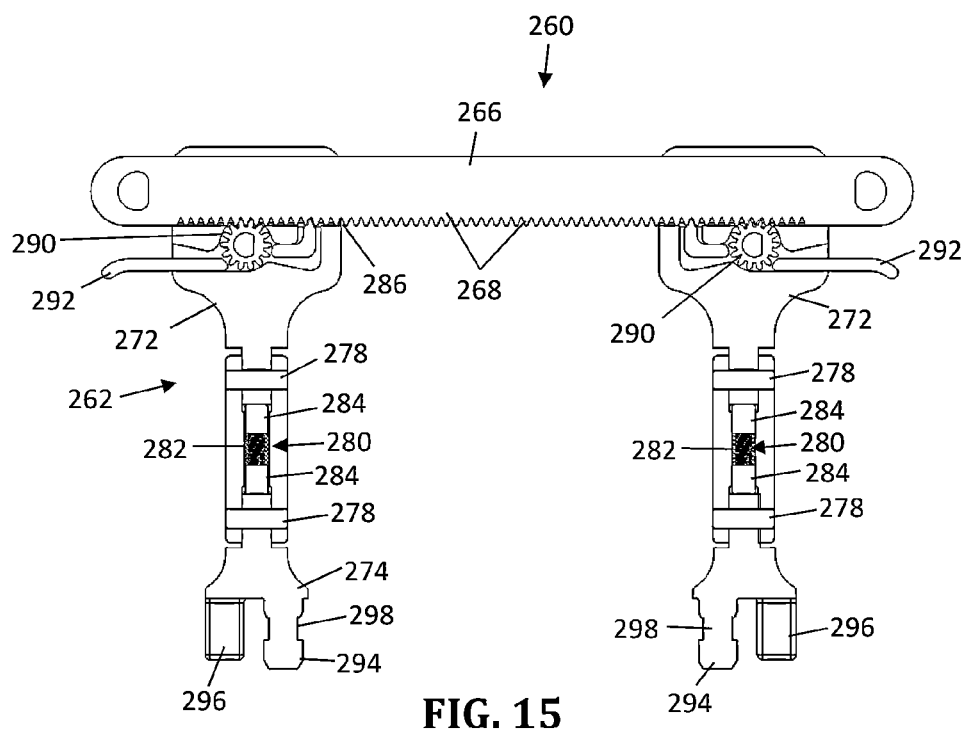
FIG. 15 is a cross section view of the retractor of FIG. 13.

Referring to FIGS. 14-15, the track 266 includes a row of teeth 268. Each end of the track 266 also includes an articulating arm post 270 which provides a connection point for rigidly attaching the second retractor 260 to the surgical table (or other stationary object) with a locking articulating arm. Either of the articulating arm posts 270 may be used depending on the orientation of the second retractor and the preference of the surgeon user.

The moving arms 262 each include a track receptacle 272 and a blade connector 274. The blade connector 274 is connected to the track receptacle 272 by pivot link 276. The pivot link 276 includes a pair of pivots 278 with one pivot 278 located on each end of the pivot link 276 to permit variability in the height of the blade connector 274 relative to the track receptacle 272 while maintaining the alignment of the blade connector 274 generally parallel to the track receptacle 272. The pivot link 276 further includes a friction mechanism 280 for preventing the blade connector 274 and the pivot link 276 from flopping around. The friction mechanism 280 includes a spring 282 with a pair of friction nubs 284 situated at each end. The friction mechanism 280 creates friction between the pivot link 276 and the blade connector 274, and between the pivot link 276 and the track receptacle 272. The friction between the pivot link 276 and each of the blade connector 274 and the track receptacle 272 is such that the application of force (e.g. directly from the user or from contact with the patient or another retractor, etc . . . ) is required to adjust the position of the blade connector 274. This way the blade connector 274 and pivot link 276 will not flop around and create a disturbance when handling the second retractor 260 and particularly when trying to position the retractor 260 in the patient.

The track receptacle 272 has a passage 286 through which the track 260 passes and which permits the moving arm 262 to translate along the track 260. The moving arms 262 are independently advanced away from the opposing moving arm by turning the knob 288. A gear 290 on the knob 288 extends into track receptacle passage 272 and engages the teeth 268 such that rotation of the knob 130 translates the moving arm 106 along the track. The movement of the moving arms 262 towards the opposing arm is prevented by a lock 292 that engages the track teeth 268. By way of example, the lock 292 may be a spring biased pawl pivotally coupled to the track receptacle 727. The knob 288 may preferably include a friction mechanism to prevent the knob from flopping around. For example, the friction mechanism (not shown) may be similar to the friction mechanism 280 that includes a spring biased friction nub in contact with a hinged portion of the knob. Arm posts 270 prohibit the track receptacle 272 from disengaging from the track 266.

The blade connector 274 includes a post 294 extending from a front side of the connector adjacent the interior side and an adjustment flange 296 extending from the front side adjacent the exterior side of the connector. The post 294 may be generally cylindrical and is dimensioned to be received within an aperture in the blade 264. A groove 298 formed around the post 294 receives a set screw engaged through the blade 294 to lock the blade 264 to the blade connector 274.

Figure 16:
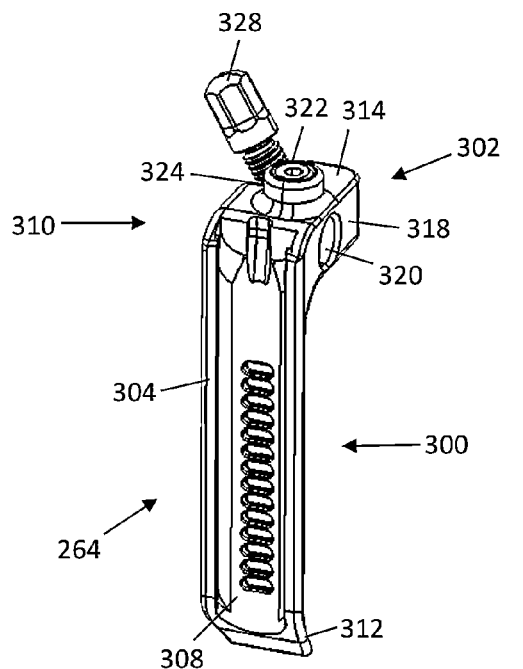
FIGS. 16-17 are front perspective and back perspective views of the cranial-caudal retractor blades, according to one example embodiment.
Figure 17:
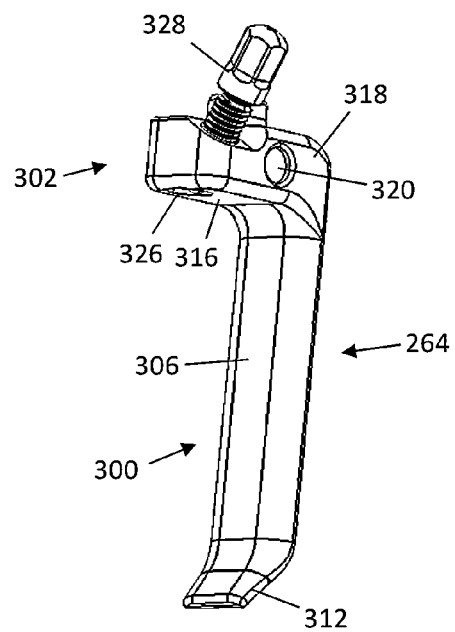
Figure 18:
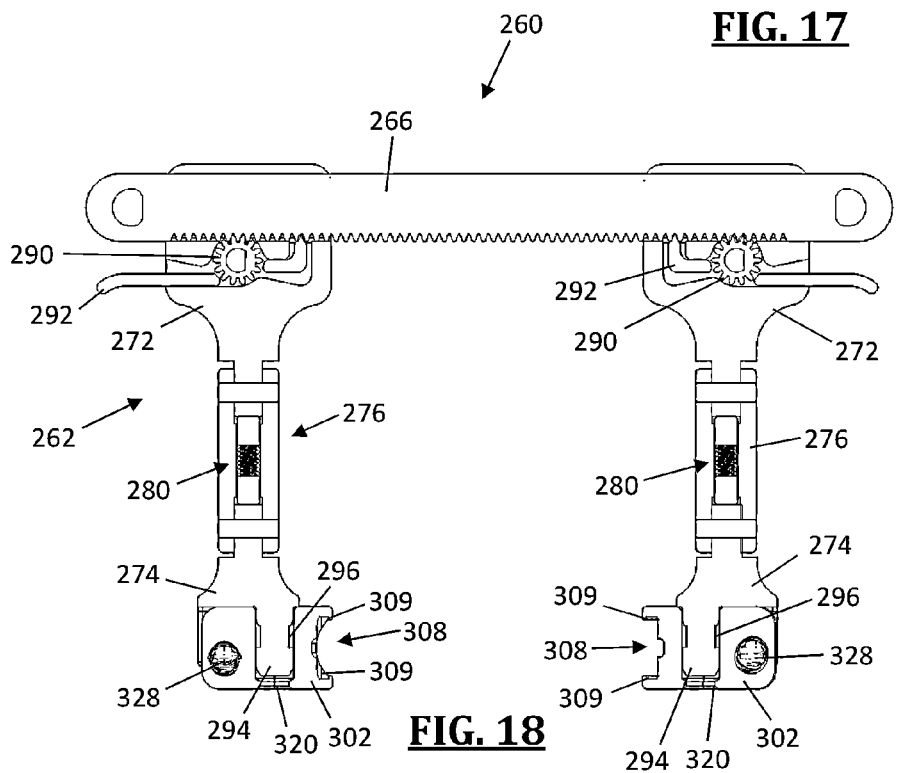
FIG. 18 is a cross section view of the retractor of FIG. 13 with the retractor blades attached.
Figures 19, 22:
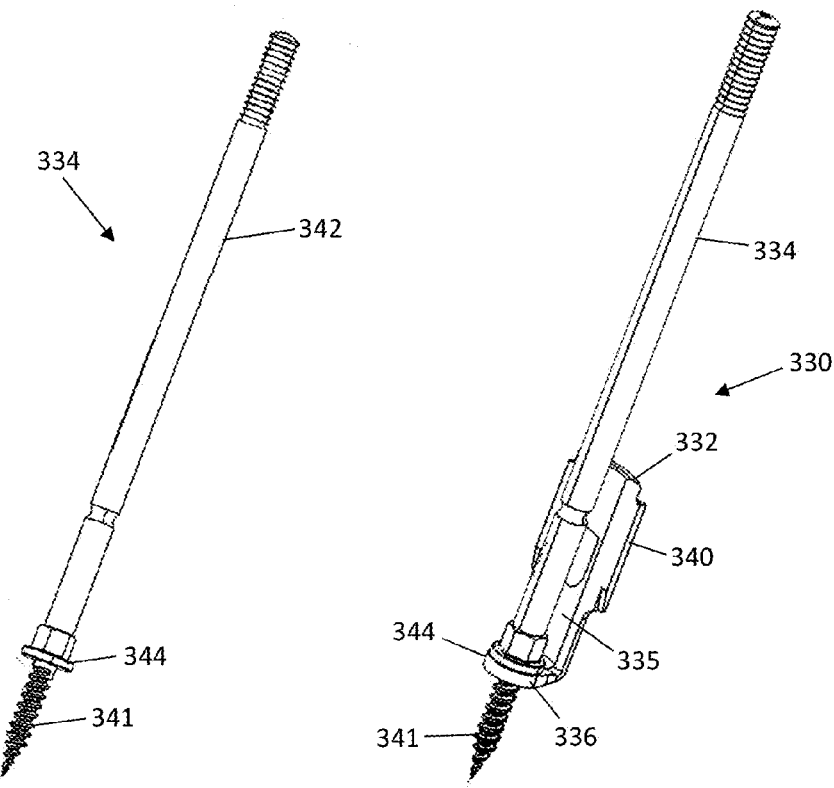
FIG. 19 is a perspective view of an anchor piece forming part of the distraction shim of FIG. 22, according to one example embodiment.
FIG. 22 is a perspective view of a distraction shim that couples to the blades of the retractor of FIG. 13.
Figures 20, 21:
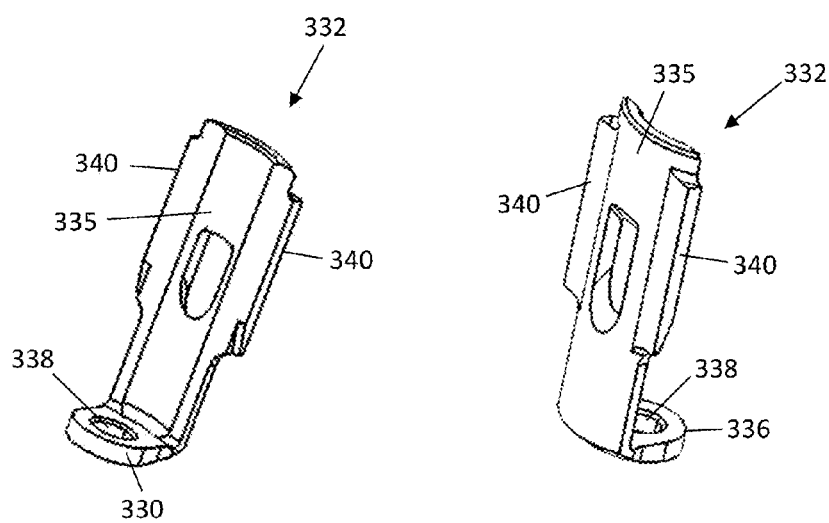
FIG. 20 is a front perspective view of a shim forming part of the distraction shim of FIG. 22, according to one example embodiment.
FIG. 21 is a back perspective view of the shim of FIG. 20.

The blades 26 4 are described with reference to FIGS. 16-17. The blades 264 each include a blade portion 300 and a connection ledge 302 that extends transversely from the proximal end 310 of the blade portion. The blade portion 300 includes an interior face 304 that faces the operative corridor and an exterior face 306 that faces and engages the body tissue adjacent the operative corridor. The interior face 302 includes a shim track 308 that slidably couples a distraction shim 330. A distal end 312 of the blade portion 300 may have any number of suitable configurations, including blunt (as illustrated) or toothed. The distal end 312 may also be angled away from the interior.

The connection ledge 302 includes a top surface 314, an under surface 316, and side surfaces 318. A first aperture 320 extends across the ledge 302 opening in at least one of the side surfaces. The first aperture 320 is dimensioned to receive the post 294 of the blade connector 274. The connection ledge includes a second aperture 322 that opens in the top surface 314 and extends into the first aperture 320. The second aperture receives a lock screw 324 that advances into the aperture 320 and mates with the cylindrical groove 298 on the post 294 to couple the blade 264 to the blade connector 274 blade while allowing free rotation about the axis of the post. The connection ledge also includes a third aperture 326 that extends through the ledge 302 at an angle and opens in the top surface 314 and undersurface 316. The third aperture 326 receives an angulation screw 328 that engages the flange 296 to cause the blade 364 to rotate around the post 294, angulating the distal end 312 of the blade 264 away from the operative corridor. By angulating one or both of the blades 264, the size of the operative corridor near the target site can be expanded without enlarging the corridor at the skin level. Additionally, with the use of distraction shims 330, the blades 264 can be angled to distract the adjacent vertebrae.

Figure 23:
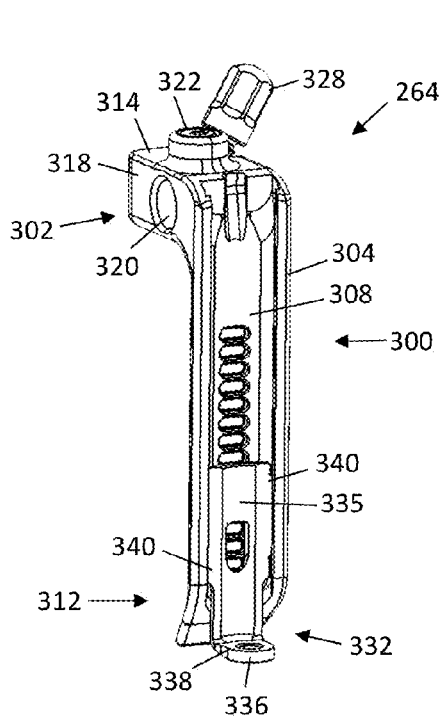
FIG. 23 is a perspective view of the shim of FIG. 20 coupled to the retractor blade of FIG. 13.
Figure 24:
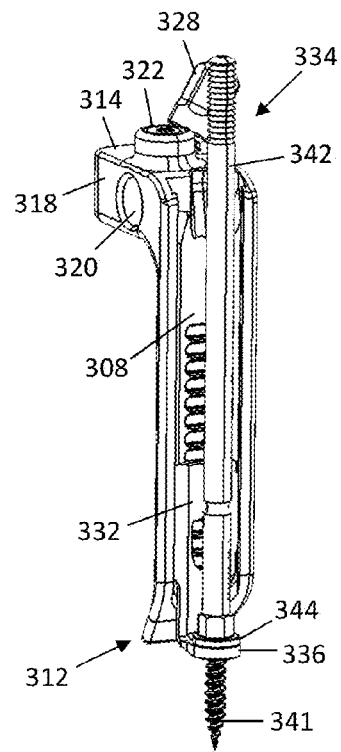
FIG. 24 is a perspective view of the entire distraction shim of FIG. 22 coupled to the retractor blade of FIG. 13.
Figure 25:
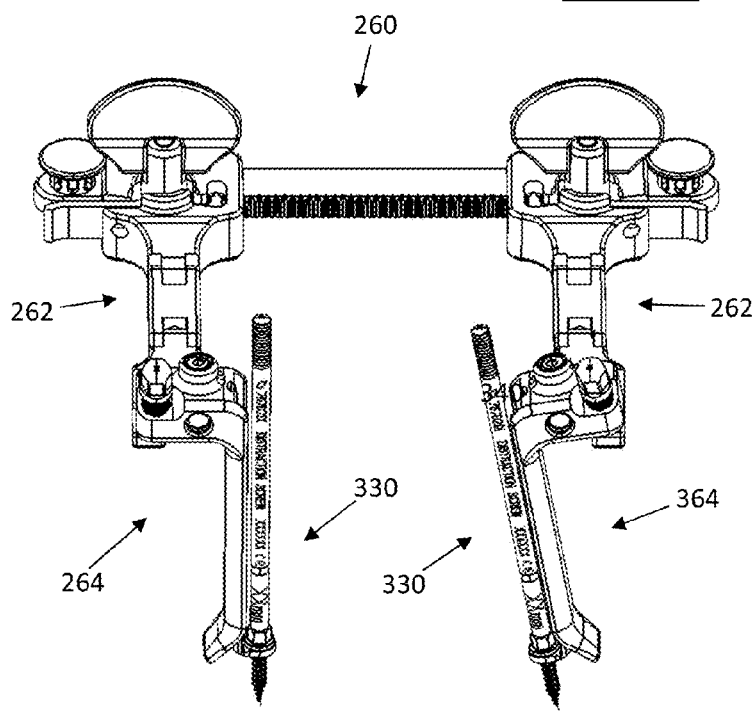
FIG. 25 is a perspective view of the retractor of FIG. 13 with a distraction shim of FIG. 22 coupled to each blade.

With reference to FIGS. 19-25, the distraction shims 330 include a shim 332 and an anchor 334. The shim 332 has a body 335 and a distal ring 336 extending generally perpendicular to the body. The distal ring 336 has an aperture 338 dimensioned to receive an anchor portion 341 of the anchor 334 and a flange. The body 335 includes a pair of wings 340 that engages grooves 309 of the shim track 308 to slidably couple the distraction shim 330 to the blade 264 (FIG. 23-24). The anchor 334 includes a distal anchor portion 340 configured to anchor into bone and separated from a shaft 342 by a flange 344. The flange 344 is larger than the aperture 338 of the distal ring 336 such that as the anchor portion 341 is advanced into to bone, the flange 344 captures the distal ring 336 against the bone, coupling the distal end 312 of the blade 264 to the vertebra. With the anchor shims 330 coupled to the blades 264 and anchored into the cranial and caudal vertebral bodies, the moving arms 262 can be operated to move the arms away from each other, distracting the space between the cranial and caudal bodies. Alternatively, or in addition, the blades 264 can be angled by operating the angulation screws 328 to also distract the space between the cranial and caudal vertebral bodies (FIG. 25).

Figure 26:
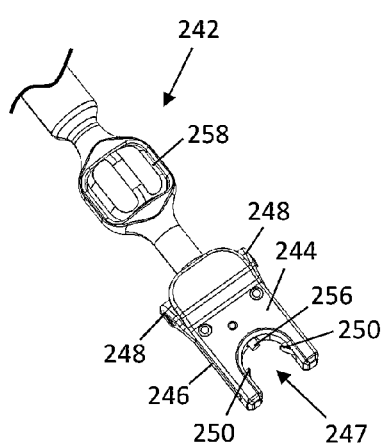
FIG. 26 is a perspective view of an articulating arm connector for rigidly coupling the retractor system of FIG. 1 to a table or similar structure.
Figure 27:
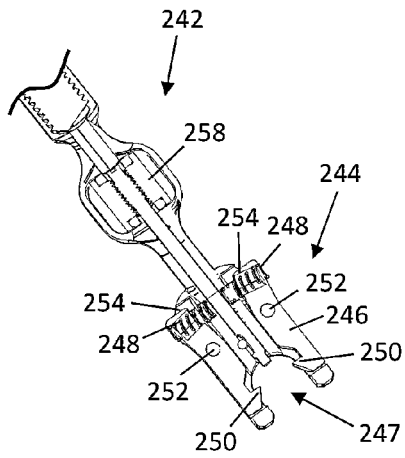
FIG. 27 is an exploded view of the articulating arm connector of FIG. 26.

FIGS. 26-27 illustrate an articulating arm connector 242 for attachment to an articulating arm post 132 of the first retractor 102. The articulating arm connector 242 attaches to a free end of the articulating arm (not shown) which may be secured at the opposite end to the surgical table or other stationary object, thus securing the position of the retractor 102 relative to the table. The articulating arm connector 242 includes an engagement head 244 with an open receptacle 247 opening in the free end of the c engagement head 244. Situated along each side of the engagement head 244 are locking arms 246 that each include a release tab 248 at one end and a locking tooth 250 at the opposite end, the release tab 248 and locking tooth 250 being separated by a pivot 252 that pivotally connects the locking arms 246 to the engagement head 244. Each of the locking arms 246 is spring loaded with a spring 254 that biases the locking tooth 250 into the open receptacle 247 where it engages with articulating arm post 132 to lock the retractor 102 to the articulating arm. The articulating arm connector also includes a translating post 256 which is threadedly coupled to a thumbwheel 258. The translating post 256 can be actuated to advance into the open receptacle 256 where it presses against the articulating arm post 132 to provide for a sturdier connection. To disengage the articulating arm connector 242, the release tabs 248 are depressed which causes the teeth 250 to withdraw into the engagement head clearing the way for removal of the articulating arm post 132 from the open receptacle 247. A tapered front edge on teeth 250 permit initial loading of the articulating arm post 132 without depressing the release tab 248 to clear the teeth out of the open receptacle 247.

Figure 28:
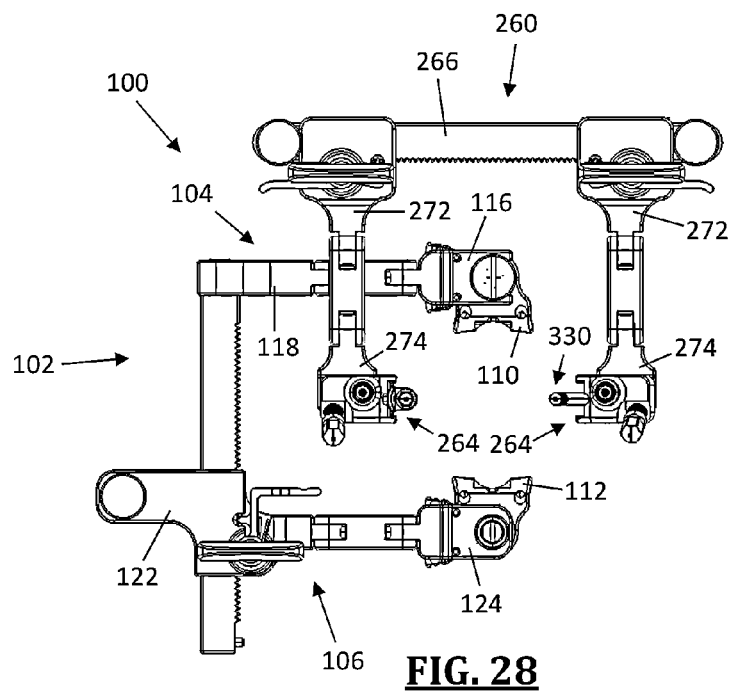
FIG. 28 is a top down view of the cervical retractor system of FIG. 1.

According to one example, a method of creating an operative corridor to a cervical target site with the cervical retractor system 100 described with reference to FIG. 28. The medial-lateral retractor 102 is positioned first. The method is initiated by attaching the side loading blade 110 to the insertion handle 218 via one tier (184, 186) of the first connection post 182. The side loading blade 110 is then retracted into the desired position with the insertion handle and then the blade 110 is locked in place with the articulating arm. To do so the articulating arm connector 242 is connected to the free tier (i.e. the tier that is not connected to the insertion handle 218) of the connection post 182. The articulating arm is then locked, fixing the position of the side loading blade 110. The insertion handle 218 is then removed to free a tier of the connection post 182 and the side loading connector 116 of the retractor body 102 is then attached to the free tier. A light, for example, a fiber optic light cable configured to mate with the shim track 180, may then be inserted into the shim track 180 of the side loading blade 110 to light the operative corridor. The top loading blade 112 is then attached to the insertion handle 218 by connecting the insertion handle 218 to the lower tier 212 of the connection post 208. The top loading blade 112 is manually retracted into the desired position and then the blade connector 274 is attached to the upper tier 210 of the connection post 208. The insertion handle 218 is removed from the lower tier 212. A second light may then be inserted into the shim track 180 of the top loading blade 112 to further light the operative corridor. The retractor 100 may then be operated to retract tissue in the medial-lateral direction. With the operative corridor established between the blades 108, the cranial-caudal retractor 260 is advanced into position. The blades 264 are first coupled to the blade connectors 274 by sliding the first aperture 320 of the connection ledge 302 onto the post 294 of each connector and locking the blades with locking screw 324. The distal ends 312 of the blades 264 are advanced through the operative corridor formed by the first retractor 102. A second articulating arm 242 is then attached to one of the articulating arm posts 270 to fix the position of the track 266. One or both of the moving arms 262 may then be operated to move the blades 264 away from each other until the exterior faces 306 of the blades engage the soft tissue surrounding the operative corridor. The moving arms may continue to be opened until the distal ends 312 of the blades rest over the cranial most and caudal most vertebral bodies of the exposure. Angulation screws 328 may also be engaged to move the distal ends 312 apart, spreading the distal end of the operative corridor without further expanding the skin incision site. Optionally, distraction shims 330 are slid down the shim tracks 180 and the anchors 334 are anchored into the cranial most and caudal most vertebral bodies. The moving arms 62 can then be separated (and/or the blades can be angulated) to distract the space between the cranial and caudal vertebrae. With the operative corridor established, the surgeon can perform the desired procedure (e.g. discectomy, fusion, disc replacement, etc . . . ).

Figure 29:
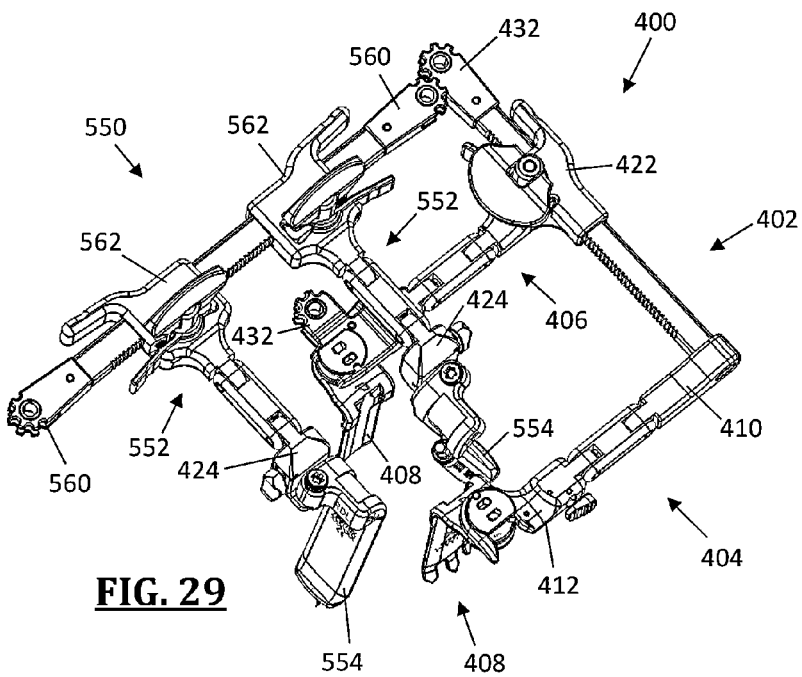
FIG. 29 is a perspective view of an anterior cervical retractor system according to a second example embodiment.

Turning to FIG. 29, a perspective view of a cervical retractor system 400 according to a second example embodiment is shown. The cervical retractor system 400 includes a first retractor 402 and a second retractor 550. According to a preferred example, the first retractor 402 is a medial-lateral retractor (i.e. tissue is retracted in the medial and lateral directions) and the second retractor 550 is a cranial-caudal retractor (i.e. tissue is retracted in the cranial and caudal directions). It is noted that while the first retractor 402 and second retractor 550 are designed to be used together, either of the first retractor 402 and the second retractor 550 may be utilized alone. By way of example, the use of the second retractor 550 may not be necessary for single level exposure. Instead, the second retractor 550 is particularly useful during multi-level procedures to prevent tissue creep into the larger exposures. The second retractor 550 can also be used to distract the disc space between the vertebrae during single level or multi-level cases.

Figure 30:
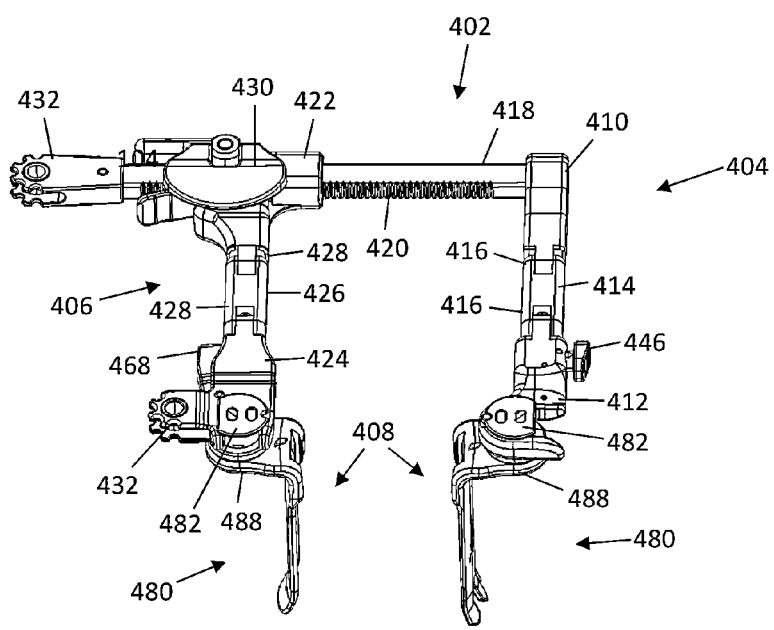
FIG. 30 is a perspective view of one example of a first, medial-lateral retractor of the retractor system of FIG. 29.
Figure 31:
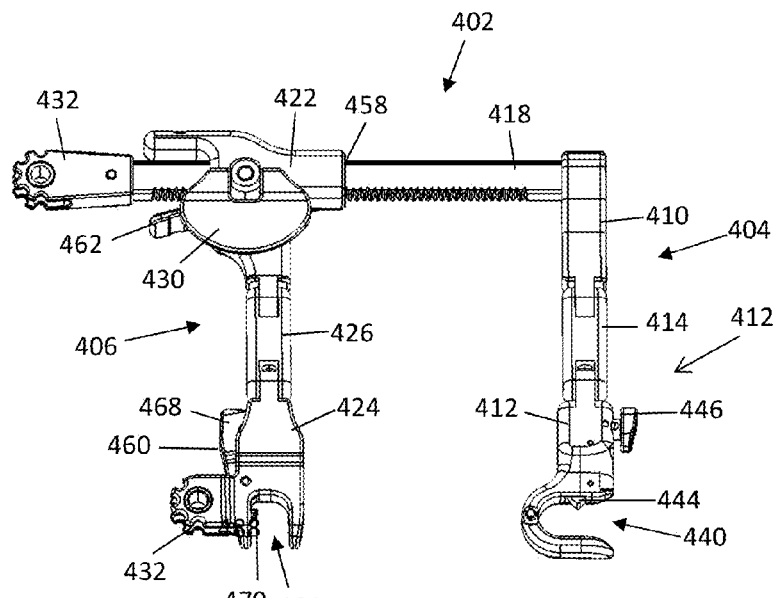
FIG. 31 is a perspective view of the retractor of FIG. 30 without the retractor blades engaged.
Figure 32:
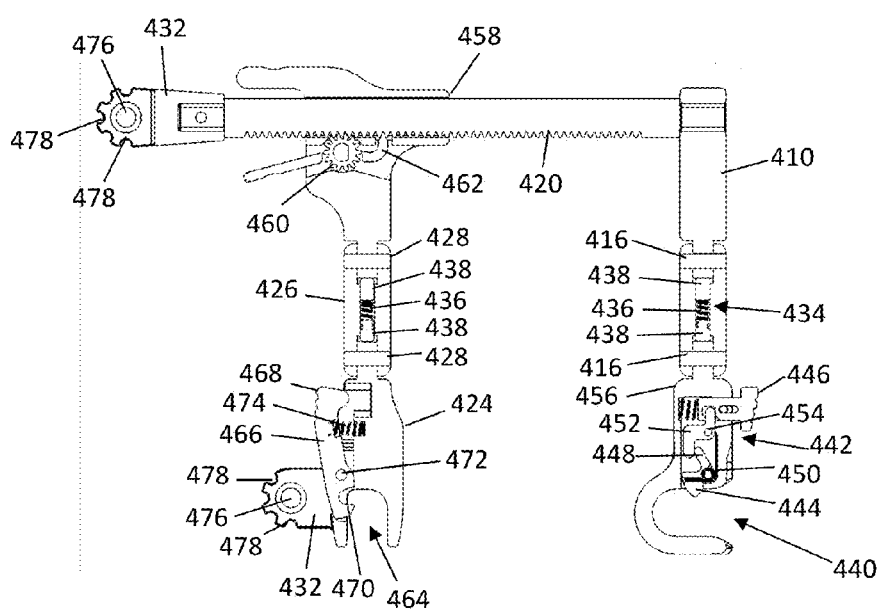
FIG. 32 is a cross section view of the retractor of FIG. 30.
Figure 40:
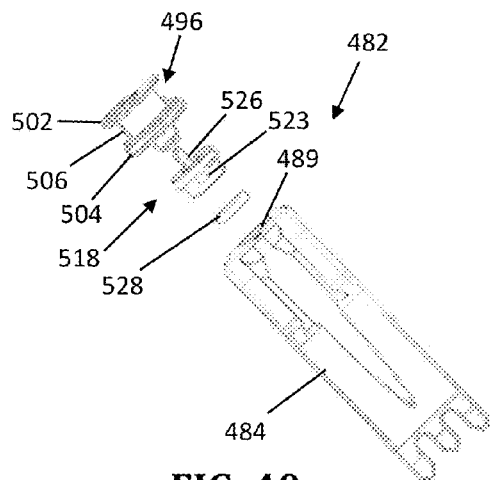
FIG. 40 is an exploded front perspective view of the retractor blade of FIGS. 33-34.
Figure 41:
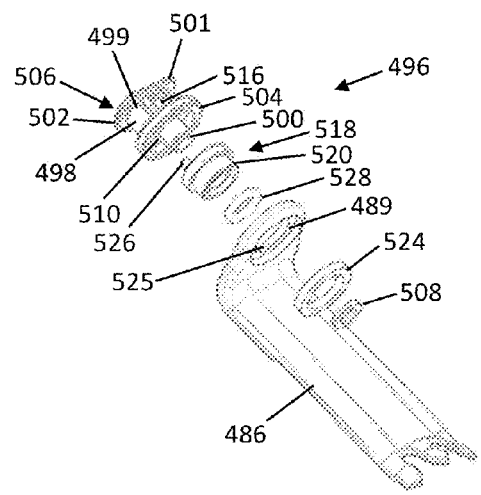
FIG. 41 is an exploded back perspective view of the retractor blade of FIGS. 33-34.
Figure 42:
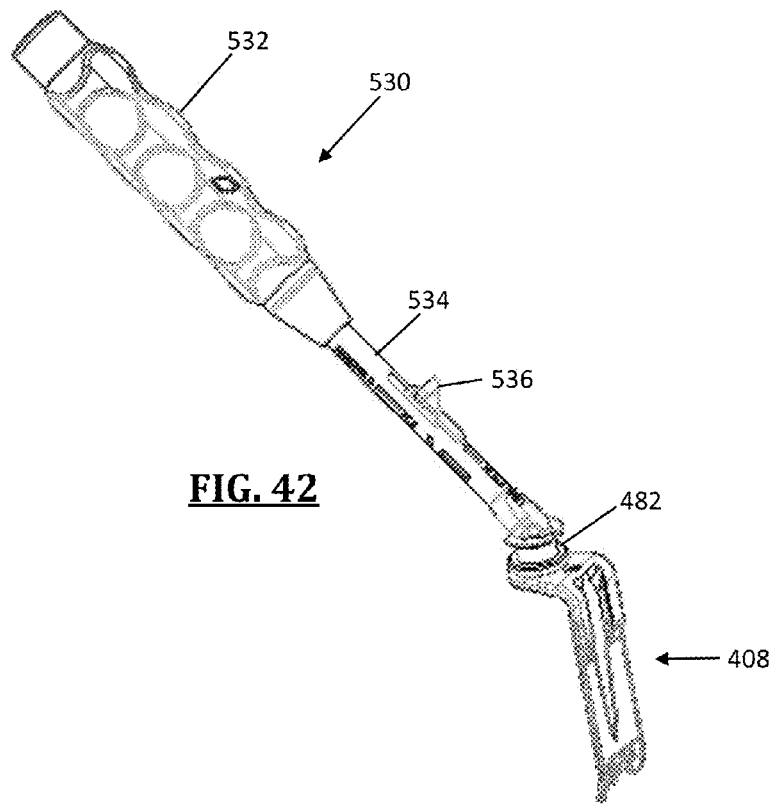
FIG. 42 a perspective view of an insertion instrument coupled with the side loading retractor blade of FIGS. 33-34, according to one example embodiment.
Figure 43:
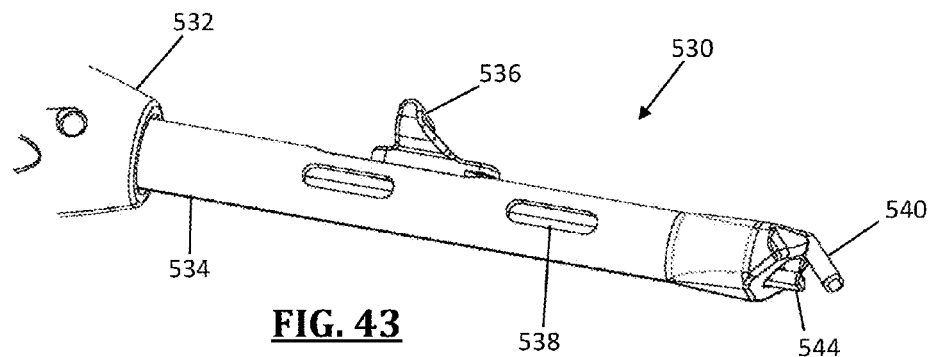
FIG. 43 is a perspective view of the insertion instrument of FIG. 42.
Figure 44:
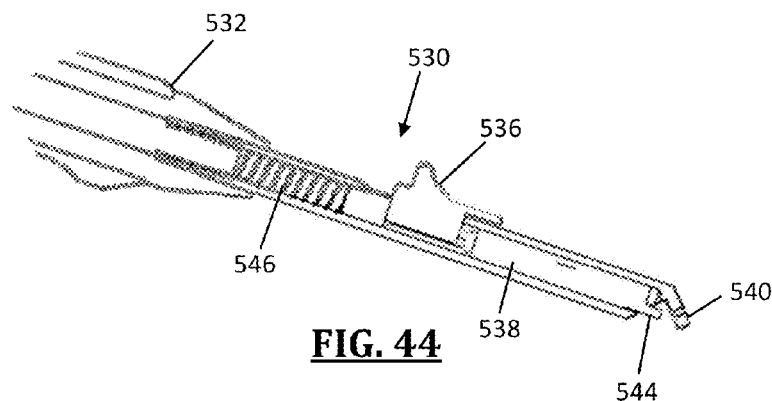
FIG. 44 is cross-section view of the insertion instrument of FIG. 42.
Figure 45:
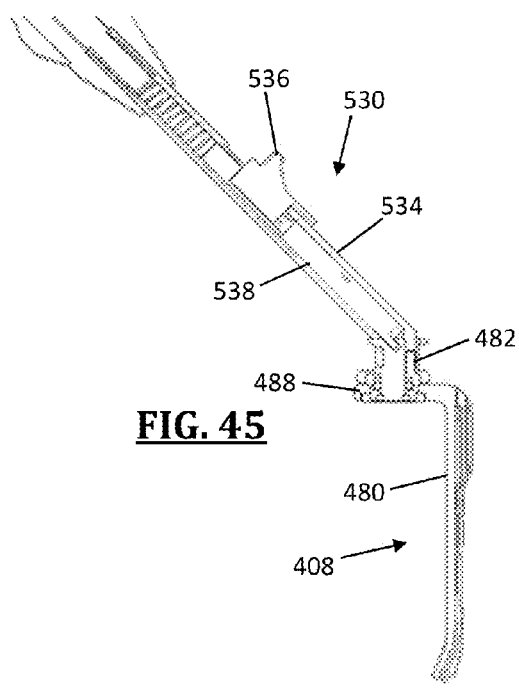
FIG. 45 is a cross-section view of the insertion instrument coupled with the side loading blade of FIG. 42.
Figure 46:
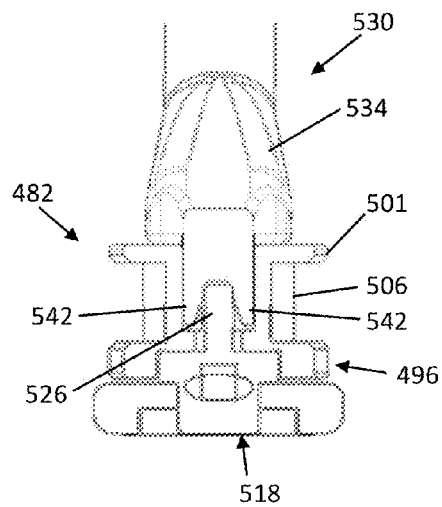
FIG. 46 is a cross-section view of the connection post of FIG. 36 coupled to the insertion instrument of FIG. 42.

With reference to FIG. 30, the first retractor 402 according to one example embodiment is depicted. The first retractor 402 includes a base arm 404 and a moving arm 406 and, a pair of side loading retractor blades 408. The base arm 404 includes a track base 410 and an inside-out connector 412 that connects one of the side loading blades 408 with aside loading inside-out connection. The inside-out connector 412 is connected to the track base 410 by a pivot link 414 having two pivots 416 such that the base arm comprises a double hinge. A first track 418 extends perpendicularly from the track base 410 of the base arm 404, the first track 418 including a row of teeth 420. The moving arm 406 is located opposite to the base arm 404. The moving arm 406 includes a first track receptacle 422 and a straight-on connector 424 that connects the other of the side loading blades 108 with a side loading straight-on connection. The straight-on connector 424 is connected to the track receptacle 422 by a pivot link 426 having two pivots 428 such that the moving arm comprises a double hinge. The moving arm 406 may be advanced along the first track 418 by means of a knob 430 to move the moving arm 406 away from the base arm 404. The moving arm 406 also includes an articulating arm receptor 432 which provides a connection point for rigidly attaching the first retractor 402 to the surgical table (or other stationary object) with a locking articulating arm.

In surgical use, according to a preferred example, the base arm 404 and the inside-out connector 412 are positioned medially (away from the surgeon) and against the esophagus and trachea. The moving arm 406 and the straight-on connector 424 are positioned laterally (closest to the surgeon). Hence, the blade 408 connected to the inside-out connector 412 may also be referred to as medial blade and the blade connected to the straight-on connector may also be referred to as the lateral blade. The retractor 402 may be then used to retract the tissue in a medial-lateral orientation.

The base arm 404 and moving arm 406 are best illustrated in FIGS. 31-34. The inside-out connector 412 is connected to the track base 410 by pivot link 414. The pivot link 414 includes a pair of pivots 416 with one pivot 416 located on each end of the pivot link 414 to permit variability in the height of the inside-out connector 412 relative to the track base 410 while maintaining the alignment of the inside-out connector 412 generally parallel to the track base 410. The pivot link 412 further includes a friction mechanism 434 for preventing the inside-out connector 412 and the pivot link 414 from flopping around. The friction mechanism 434 includes a spring 436 with a pair of friction nubs 438 situated at each end. The friction mechanism 434 creates friction between the first pivot link 414 and the inside-out connector 412, and between the pivot link 414 and the track base 410. The friction between the pivot link 414 and each of the inside-out connector 412 and the track base 410 is such that the application of force (e.g. directly from the user or from contact with the patient or another retractor, etc . . . ) is required to adjust the position of the inside-out connector 412. This way the inside-out connector 412 and pivot link 414 will not flop around and create a disturbance when handling the retractor 402 and particularly when trying to position the retractor 402 in the patient.

The inside-out connector 412 includes an open receptacle 440 opening in the outside side of the connector 412 and a lock 442. The lock 442 includes a locking tooth 444 which is spring biased, via spring 456, to extend into the open receptacle 442. A release tab 446 is coupled to the locking tooth 444 and withdraws the locking tooth 444 from the open receptacle 440 when depressed to permit removal of the blade 408. The locking tooth 444 has a lever arm 448 connected to tooth on opposite sides of a pivot 450. A z-shaped center link 452 is situated between the release tab 446 and the lever arm 448. At one end the center link 452 is received within a recess in the release tab 446 such that depressing the release tab causes the center link 452 to swing about the pivot 454. At the opposite end, the center link 452 rests adjacent to the lever arm 448 such that when the center link swings around the pivot 454 the lever arm 448 is moved toward the outside side and the tooth 444 moves into the connector. A tapered front edge on the locking tooth 444 permits loading of the blade 408 without clearing the tooth 444 out of the open receptacle 440. The center link 448 allows the release tab 446 to remain still during blade connection.

The straight-on connector 424 is connected to the track receptacle 422 by pivot link 426. The pivot link 426 includes a pair of pivots 428 with one pivot 428 located on each end of the pivot link 426 to permit variability in the height of the straight-on connector 424 relative to the track receptacle 422 while maintaining the alignment of the straight-on connector 424 generally parallel to the track receptacle 422. The pivot link 426 further includes a friction mechanism 434 for preventing the straight-on connector 424 and the pivot link 426 from flopping around. The friction mechanism 434 includes a spring 436 with a pair of friction nubs 438 situated at each end. The friction mechanism 434 creates friction between the first pivot link 426 and the straight-on connector 424, and between the pivot link 426 and the track receptacle 422. The friction between the pivot link 426 and each of the straight-on connector 424 and the track receptacle 422 is such that the application of force (e.g. directly from the user or from contact with the patient or another retractor, etc . . . ) is required to adjust the position of the straight-on connector 424. This way the straight-on connector 424 and pivot link 426 will not flop around and create a disturbance when handling the retractor 402 and particularly when trying to position the retractor 402 in the patient.

The track receptacle 422 has a passage 458 through which the track 418 passes and which permits the moving arm 406 to translate along the track 418. The moving arm 406 is advanced away from the base arm 404 by turning the knob 430. A gear 460 on the knob 430 extends into track receptacle passage 458 and engages the teeth 420 such that rotation of the knob 430 translates the moving arm 406 along the track away from the base arm 404. Movement of the moving arm 406 towards the base arm 404 is prevented by a lock 462 that engages the track teeth 420 in such a way that motion away from the base arm 406 is permitted while motion towards the base arm is inhibited. By way of example, the lock 462 may be a spring biased pawl pivotally coupled to the track receptacle. The knob 430 may preferably include a friction mechanism to prevent the knob 430 from flopping around. For example, the friction mechanism (not shown) may be similar to the friction mechanism 434 that includes a spring biased friction nub in contact with a hinged portion of the knob. The articulating arm receptor 432 on the end of the track 418 prohibits the track receptacle 422 from disengaging from the track 418.

The straight-on connector 424 includes an open receptacle 464 opening in the front end of the connector 424. Situated along the outside side of the straight-on connector 424 is a locking arm 466 that includes a release tab 468 at one end and a locking tooth 470 at the opposite end, the release tab 468 and locking tooth 470 being separated by a pivot 472 that pivotally connects the locking arm 466 to the connector 424. The locking arm 466 is spring loaded with a spring 474 that biases the locking tooth 470 into the open receptacle 464 where it engages with connection post of the blade 408 to lock the blade 408 to the connector. To disengage the blade 408 from the straight-on connector 424, the release tab 468 is depressed which causes the tooth 470 to withdraw into the connector clearing the way for removal of the connection post from the open receptacle 464. A tapered front edge on tooth 470 permits loading of the blade 108 without depressing the release tab 468 to clear the tooth 470 out of the open receptacle 464. The outside side of the straight-on connector 424 also includes an articulating arm receptacle 432 which allows the roles of the moving arm 406 and the base arm 404 to be reversed. That is, with an articulating arm coupled to the articulating arm receptor 432 on the moving arm 404 rather than the receptor on the track 418, rotating the knob 430 on the track receptacle 422 causes the track 418 to move though the track receptacle, pushing the base arm 404 away from the moving arm 406. The articulating arm receptor 432 includes a receptacle 476 and a plurality of cutouts 478 situated around the arced upper and lower outer edges of the receptor 432.

FIGS. 33-35 depict the side loading blade 408. The side loading blade 408 is configured to couple with both the straight-on connector 424 and the inside-out connector 412. The side loading blade 408 includes a blade portion 480 and a connection post 482. The blade portion 480 includes an interior face 484 that faces the operative corridor, an exterior face 486 that faces and engages the body tissue adjacent the operative corridor, a ledge 488 that extends transversely away from the exterior face 486 at a proximal end 490 of the blade portion, and a distal end 492. The interior face 484 includes a light track 494 at the proximal end 490 that slidably couples a lighting element (not shown). The side loading blade 408 may also include at least one suction channel (not shown) designed to receive and hold a suction instrument within the operative corridor. The distal end 492 may have any number of suitable configurations, including blunt or toothed. The distal end 492 may also be angled away from the interior.

With reference to FIGS. 35-41, the connection post 482 is coupled to the ledge 488 and serves as an attachment structure for coupling the side loading blade 408. The connection post 482 is configured give the blade 408 the ability to mate with the retractor while still allowing a limited amount of rotation to best seat the blade 408 within the soft tissue (e.g. self align) and thereby reduce pressure points and potential for damage to the tissue. The connection post 482 includes an upper post 496 having a generally cylindrical body 498 with a flat face 499, an inferior cylinder 500 extending down from the body, an upper surface 501 with a flange 502, a lower flange 504 defining a connection groove 506 around the body with the upper flange 502, and an upper post retaining ring 508. A rotation limiting slot 510, handle engagement slot 512, locking slot 514, and locking recess 516 are also situated in the upper post 496. The connection post 482 also includes lower post 518 having a body 520, an inferior cylinder 522, a lower post retaining ring 524, and a rotation limiting extension 526. To provide the limited rotation ability of blade 408, the lower post 518 is secured to the blade ledge 488 such that it cannot rotate. The inferior cylinder 522 is passed through an aperture 489 in the ledge from the top and the lower post retaining ring 524 is welded to the cylinder 522. A dimple 523 on the outer surface of the inferior cylinder 522 mates with a recess 525 in the aperture 488 to prevent rotation of the lower post relative to the ledge 488.

The inferior cylinder 500 of the upper post 496 is passed through the center of the lower post 518 and the upper post retaining ring 508 is welded to the inferior cylinder 500 of the upper post underneath the lower post. A rotation limiting extension 526 extends from the lower post and is received in a rotation limiting slot 510 within the upper post body 498. When the upper post is connected to either the inside-out connector 412 or straight on connector 424, the blade is able to rotate until the extension 526 contacts either side of the rotation limiting slot 510. An O-ring 528 is situated in an interior groove 530 in the lower post 518 and is squeezed between lower post 518 and upper post 496. The O-ring generates friction which prevents sloppy rotation between upper post 496 and lower post 518. The handle engagement slot 512 and locking slot 514 provide for coupling of an insertion instrument to the upper surface 501 of the connection post 482 such that the blade 408 can be coupled to the insertion instrument and retractor at the siem time. To lock the upper post 496 to the inside-out connector 412 of the base arm 404, the connection groove 506 is advanced into the open receptacle 440 with the flat face 499 facing the outside side of the connector. When the upper post 496 is fully received within the open recetacle 440, the locking tooth 444 will extend into the open receptacle across a portion of the flat face 499, blocking passage of the upper post 496 back in the opposite direction until the tooth 444 is withdrawn from the open receptacle. To lock the upper post 496 to the straight-on connector 424 of the moving arm 406, the connection groove 506 is advanced into the open receptacle 464 with the flat face 499 again facing the outside side. When the upper post 496 is fully received within the open receptacle 464, the locking tooth 470 will catch inside the locking recess 516 formed in the flat face 499, preventing movement of the upper post 496 back in the opposite direction until the tooth 470 is withdrawn from the open receptacle 464.

FIGS. 42-46 illustrate an insertion instrument 530 for advancing the side loading blade 408 to cervical target site. The insertion instrument 530 comprises a grip 532, an outer shaft 534, a lever 536, an inner shaft 538 and an engagement prong 540. The engagement prong 540 is acutely angled relative to the outer shaft 534 and is dimensioned to be received within the handle engagement slot 512. As best viewed in FIG. 46, the engagement prong has two chamfered ends 542 that engage the rotation limiting post 526, guiding the post 526 to the center and prohibiting rotation of the blade when connected to the insertion instrument 530. The inner shaft 538 has a locking post 544 that extends towards the engagement prong 540 and is spring biased, via spring 546, to the locked position where it extends from the outer shaft 534. The locking post is dimensioned to be received in the angled locking slot 514 of the upper post 496, and when received in the locking slot 514 after the engagement prong 540 is received in the engagement slot 512, the blade 408 is retained on the insertion instrument 530. The lever 536 is attached to the inner shaft 534 such that pulling the lever back towards the grip 532 disengages the locking post 544 from the locking slot 514, allowing the insertion instrument to be removed from the blade 408.

Figure 47:
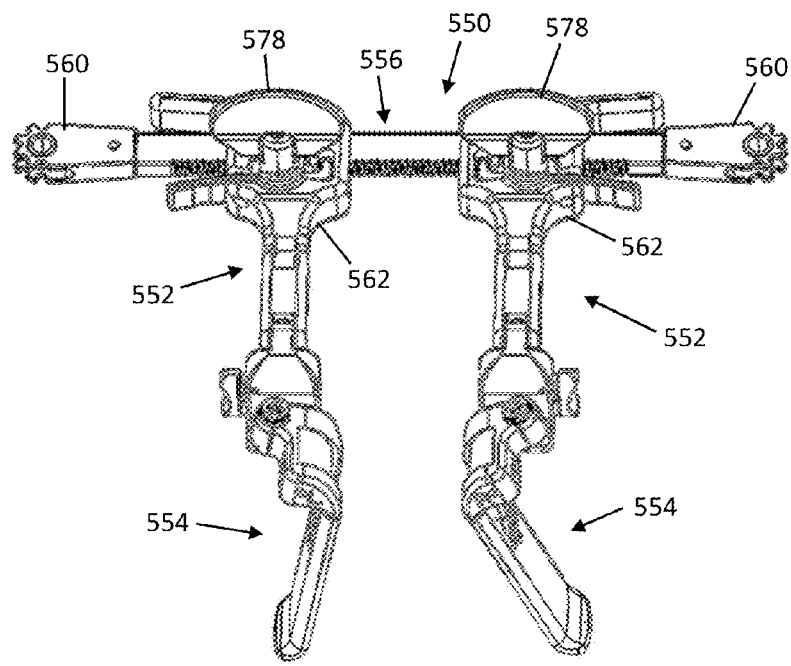
FIG. 47 a perspective view of one example of a second, cranial-caudal retractor of the retractor system of FIG. 29.

With reference to FIG. 47, the second retractor 550 according to one example embodiment is depicted. The second retractor 550 includes a pair of moving arms 552, a pair of blades 554, and a track 556 along which the moving arms 552 translate. In surgical use, according to a preferred example, one moving arm 552 and blade 554 is placed cranially and the other moving arm 552 and blade 554 are placed caudally, thus, the second retractor 550 may also be referred to as the cranial-caudal retractor. As mentioned above, the second retractor 552 may be especially useful to prevent tissue creep during multilevel procedures and during procedures in which distraction of the vertebral bodies is required. The moving arms 552 are identical, but mirror images of each other. Likewise, the blades 554 are identical, but mirror images of each other. Accordingly, the second retractor can be positioned in either of a left (i.e. track is on left) or right (i.e. track is on right) position, depending on the orientation of the first retractor 400 and/or the surgeons preference.

Figure 48:
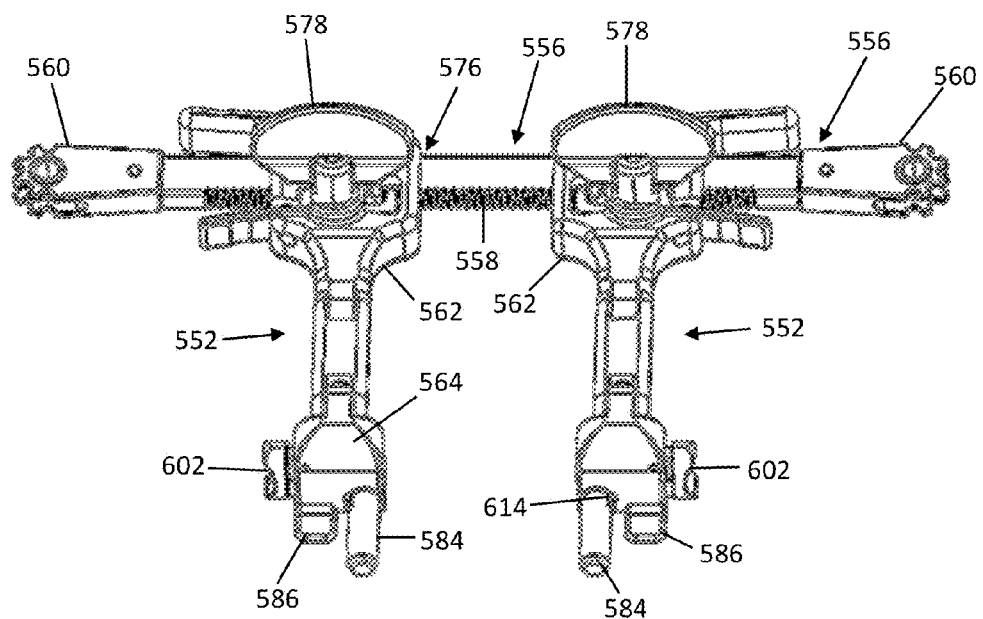
FIG. 48 a perspective view of the retractor of FIG. 47 without the retractor blades engaged.
Figure 49:
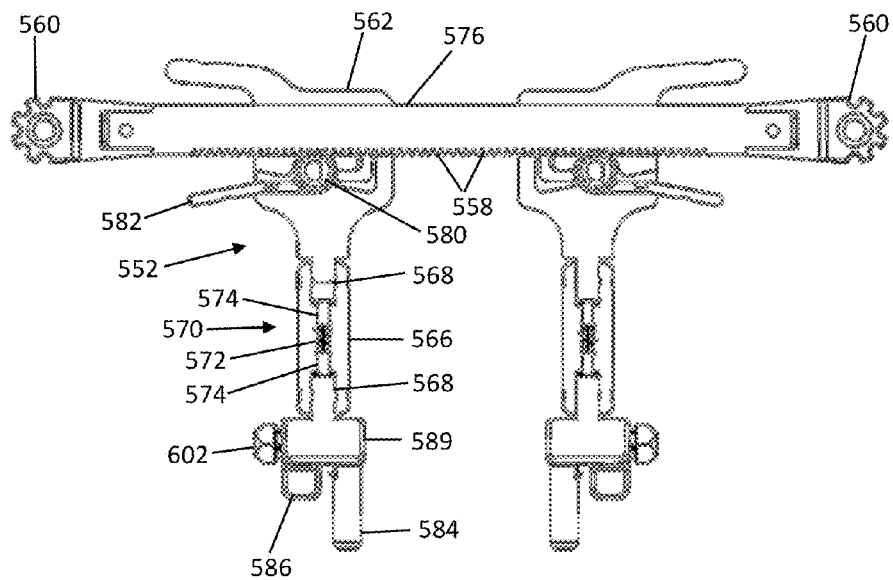
FIG. 49 is a cross section view of the retractor of FIG. 47.

Referring to FIGS. 48-49, the track 556 includes a row of teeth 558. Each end of the track 556 also includes an articulating receptor 560 which provides a connection point for rigidly attaching the second retractor 550 to the surgical table (or other stationary object) with a locking articulating arm. Either of the articulating arm posts 560 may be used depending on the orientation of the second retractor and the preference of the surgeon user.

The moving arms 552 each include a track receptacle 562 and a blade connector 564. The blade connector 564 is connected to the track receptacle 562 by pivot link 566. The pivot link 566 includes a pair of pivots 568 with one pivot 568 located on each end of the pivot link 566 to permit variability in the height of the blade connector 564 relative to the track receptacle 562 while maintaining the alignment of the blade connector 564 generally parallel to the track receptacle 562. The pivot link 566 further includes a friction mechanism 570 for preventing the blade connector 564 and the pivot link 566 from flopping around. The friction mechanism 570 includes a spring 572 with a pair of friction nubs 574 situated at each end. The friction mechanism 570 creates friction between the pivot link 566 and the blade connector 564, and between the pivot link 566 and the track receptacle 562. The friction between the pivot link 566 and each of the blade connector 564 and the track receptacle 562 is such that the application of force (e.g. directly from the user or from contact with the patient or another retractor, etc . . . ) is required to adjust the position of the blade connector 564. This way the blade connector 564 and pivot link 566 will not flop around and create a disturbance when handling the second retractor 550 and particularly when trying to position the retractor 550 in the patient.

The track receptacle 562 has a passage 576 through which the track 556 passes and which permits the moving arm 552 to translate along the track 556. The moving arms 552 are independently advanced away from the opposing moving arm by turning the knob 578. A gear 580 on the knob 578 extends into track receptacle passage 576 and engages the teeth 558 such that rotation of the knob 578 translates the moving arm 552 along the track 556. The movement of the moving arms 552 towards the opposing arm is prevented by a lock 582 that engages the track teeth 558. By way of example, the lock 582 may be a spring biased pawl pivotally coupled to the track receptacle 562. The knob 578 may preferably include a friction mechanism to prevent the knob from flopping around. For example, the friction mechanism (not shown) may be similar to the friction mechanism 570 that includes a spring biased friction nub in contact with a hinged portion of the knob. Articulating arm receptors 560 prohibit the track receptacles 562 from disengaging from the track 556.

Figure 50:
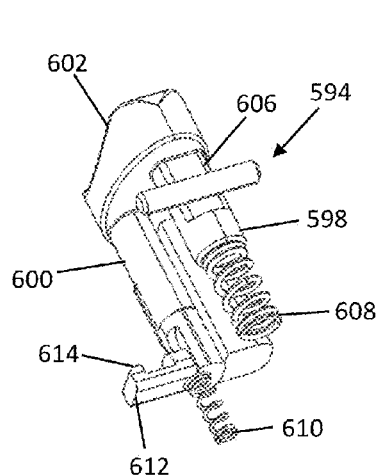
FIG. 50 is a perspective view of a lock of the retractor of FIG. 47 shown removed from the retractor arm for illustrative purposes, according to one example embodiment.
Figure 51:
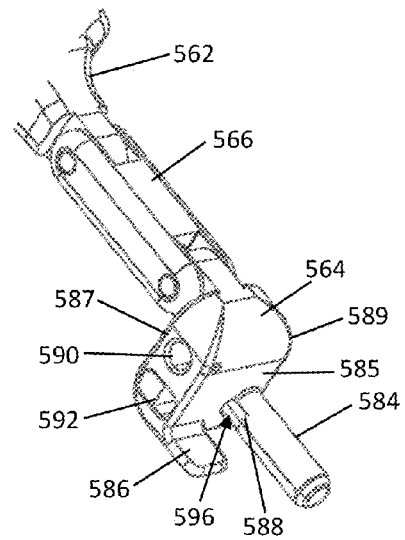
FIG. 51 is a perspective view of a blade connector of the retractor of FIG. 47 with the lock of FIG. 50 removed for illustrative purposes.

As best viewed in FIGS. 50-51, the blade connector 564 includes a post 584 extending from a front side 585 of the connector adjacent the interior side 589 and an adjustment flange 586 extending from the front side 585 adjacent the exterior side 587 of the connector. The post 584 may be generally cylindrical and is dimensioned to be received within an aperture in the blade 554. The post 584 includes an interior cavity 596 with an opening 588 adjacent the front side 585 dimensioned to receive a locking tooth 614 of a lock 594. The connector 564 also includes an upper channel 590 and a lower channel 592 opening in the exterior face 587 and dimensioned to receive portions of the lock 594. The lower channel 590 connects with the interior cavity 591. The lock 594 includes an upper post 598 dimensioned to slide within the upper channel 590 and a lower post 600 dimensioned to slide within the lower channel 592. A side arm 612 extends perpendicularly from the lower post 600 into the interior cavity 596 of the connector post 584. A locking tooth 614 on the end of the side arm 612 extends through the opening 588 and engages a groove (not shown) within the blade aperture 634 to lock the blade 554 to the connector 564. The upper post 598 and lower post 600 are connected outside the connector 564 via release tab 602. A pin 604 nestles in a recess 606 of the upper post 598 to prevent maintain the connection between the lock 594 and the connector 564 and springs 608 and 610, situated in the upper channel 598 and lower channel 600, respectively, bias the lock 594 in the locked position. Depressing the release tab 602 drives the upper post 598 and lower post 600 into the upper and lower channels, withdrawing the locking tooth 614 into the interior cavity 596, freeing the blade 554 for removal from the connector 564. A tapered front side of the locking tooth 614 permits the blade to be advanced onto the connector 564 without depressing the release tab 602 to withdraw the locking tooth 614 into the cavity 596.

Figure 52:
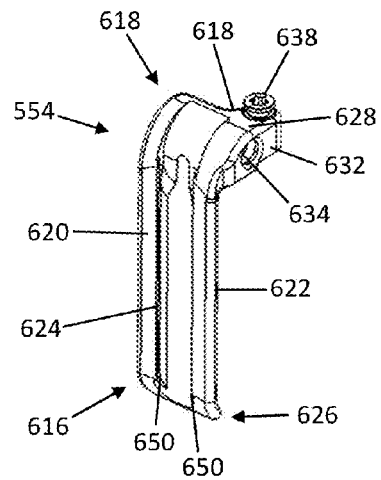
FIGS. 52-53 are front perspective and back perspective views of the cranial-caudal retractor blades of the retractor of FIG. 47, according to one example embodiment.
Figure 53:
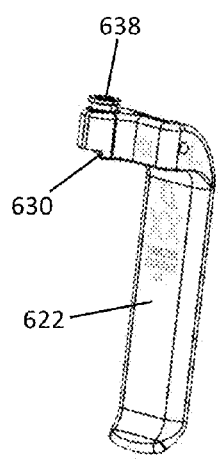
Figure 54:
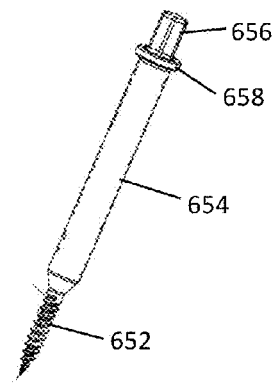
FIG. 54 is a perspective view of an anchor piece forming part of the distraction shim of FIG. 55, according to one example embodiment.
Figure 55:
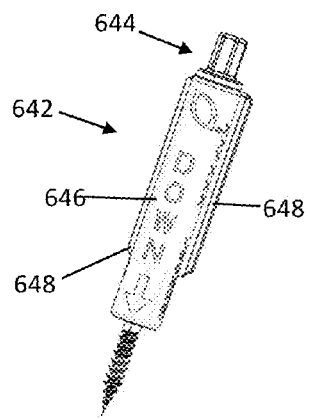
FIG. 55 is a perspective view of one example embodiment of a distraction shim that couples to the blades of the retractor of FIG. 47.
Figure 56:
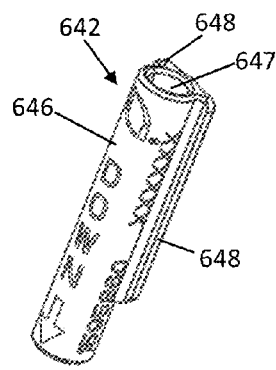
FIGS. 56-57 are front perspective and back perspective views of a shim forming part of the distraction shim of FIG. 55.
Figure 57:
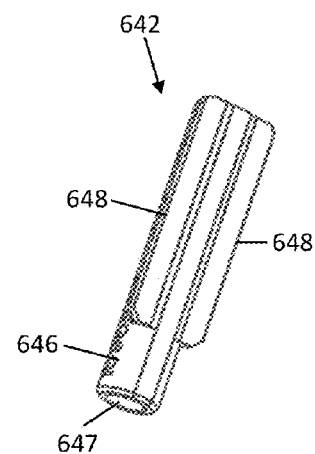

The blades 554 are described with reference to FIGS. 52-53. The blades 554 each include a blade portion 616 and a connection ledge 618 that extends transversely from the proximal end 618 of the blade portion. The blade portion 616 includes an interior face 620 that faces the operative corridor and an exterior face 622 that faces and engages the body tissue adjacent the operative corridor. The interior face 620 includes a shim track 624 that slidably couples a distraction shim 640. A distal end 626 of the blade portion 616 may have any number of suitable configurations, including blunt (as illustrated) or toothed. The distal end 626 may also be angled away from the interior.

The connection ledge 618 includes a top surface 628, an under surface 630, and an inside surface 632. An aperture 634 extends across the ledge 618 and opens in the interior side surface. The aperture 634 receives the connector post 584 and includes an inner groove that engages the locking tooth 614. The connection ledge 618 also includes a second aperture 636 that extends through the ledge 618 and opens in the top surface 628 and undersurface 630. The second aperture 336 receives an angulation screw 638 that engages the flange 586 to cause the blade 554 to rotate around the post 584, angulating the distal end 626 of the blade 554 away from the operative corridor. By angulating one or both of the blades 554, the size of the operative corridor near the target site can be expanded without enlarging the corridor at the skin level. Additionally, with the use of distraction shims 640, the blades 554 can be angled to distract the adjacent vertebrae.

Figure 58:
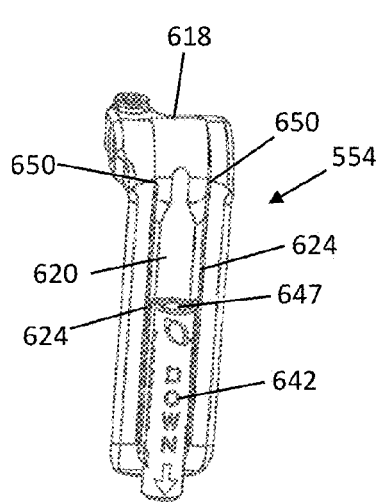
FIG. 58 is a perspective view of the shim of FIGS. 56-57 coupled to the retractor blade of FIG. 47.
Figure 59:
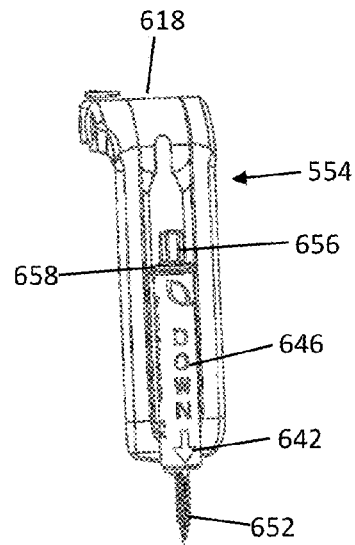
FIG. 59 is a perspective view of the entire distraction shim of FIG. 55 coupled to the retractor blade of FIG. 47.
Figure 60:
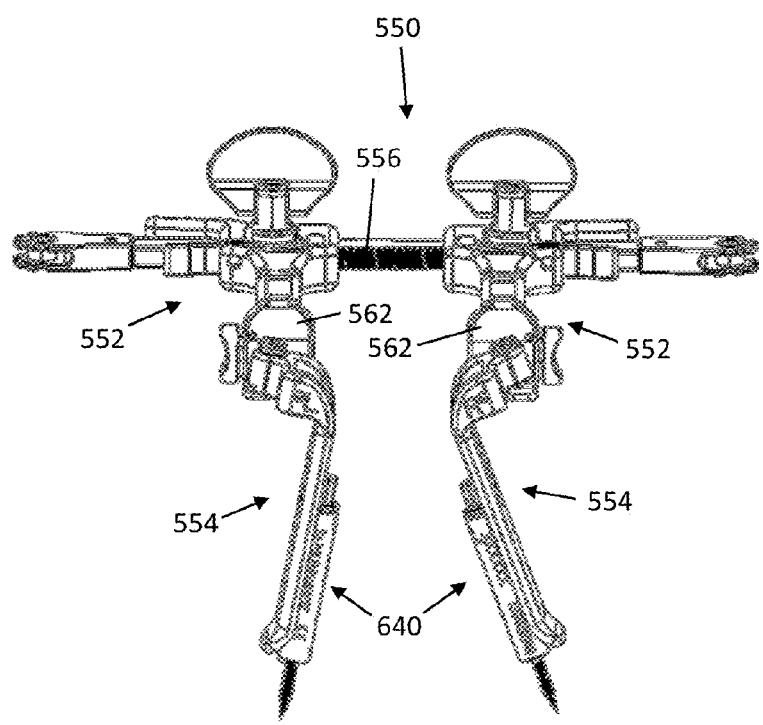
FIG. 60 is a perspective view of the retractor of FIG. 47 with a distraction shim of FIG. 55 coupled to each blade.

With reference to FIGS. 54-59, the distraction shims 640 include a shim 642 and an anchor 644. The shim 642 has a tubular body 646 with a passage 647 dimensioned to receive the anchor 644 therethrough. The body 636 includes a pair of wings 648 that engages grooves 650 of the shim track 624 to slidably couple the distraction shim 640 to the blade 554 (FIG. 58-59). The anchor 644 includes a distal anchor portion 652 configured to anchor into bone, a shaft 654, and a head 656 separated from the shaft by a flange 658. The flange 658 is larger than the passage 647 such that as the anchor portion 652 is advanced into to bone, the shim 640 is fully seated in the shim track 624, coupling the distal end 626 of the blade 554 to the vertebra. With the anchor shims 640 coupled to the blades 554 and anchored into the cranial and caudal vertebral bodies, the moving arms 552 can be operated to move the arms away from each other, distracting the space between the cranial and caudal bodies. Alternatively, or in addition, the blades 554 can be angled by operating the angulation screws 638 to also distract the space between the cranial and caudal vertebral bodies (FIG. 60).

Figure 61:
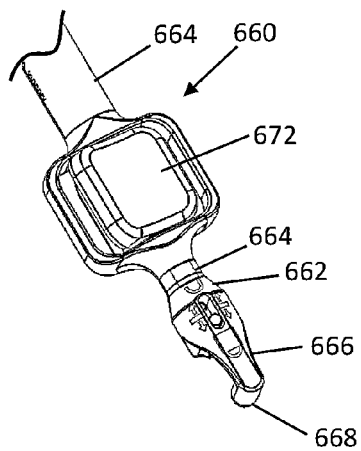
FIG. 61-62 are top perspective and bottom perspective views an articulating arm connector for rigidly coupling the retractor system of FIG. 29 to a table or similar structure.
Figure 62:
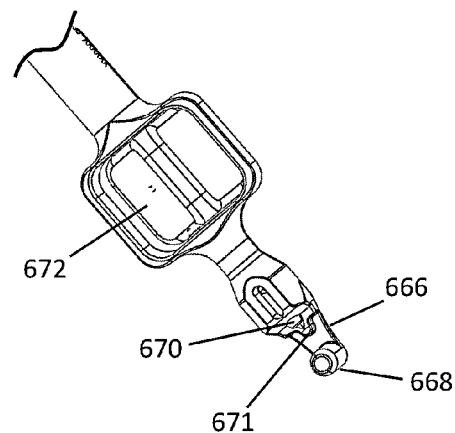
Figure 63:
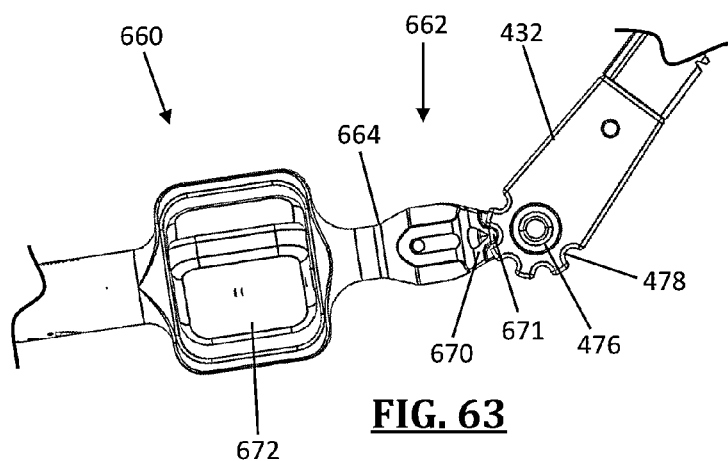
FIG. 63 is a bottom perspective view of the articulating arm connector of FIGS. 61-62 coupled to an articulating arm receptor of the retractor system of FIG. 29.

FIGS. 61-63 illustrate an articulating arm connector 660, according to a second example embodiment, for attachment to an articulating arm receptors 432 and 560 the first and second retractors 402 and 550. The articulating arm connector 660 attaches to a free end of the articulating arm (not shown) which may be secured at the opposite end to the surgical table or other stationary object, thus securing the position of the retractors relative to the table. The articulating arm connector 660 includes an engagement head 662 with an outer shaft 664, a finger 666 extending from the outer shaft and a finger post 668 extending perpendicularly down from the finger 666, and a locking shaft 670 situated within the outer shaft. A knob 672 translates the locking shaft in and out of the outer shaft. A protrusion 671 extending from the outer shaft 664 just below the finger 666 complementarily mates with one of the cutouts on the receptor when the finger 666 is inserted into the receptacle. The engagement of the protrusion 671 and cutout prevent rotation of the articulating arm connector 660 relative to the receptor 432 or 560. The protrusion may be mated with any of the cutouts to change the angular orientation of the connector 660 relative to the retractor. With the finger 666 positioned in the receptacle, the locking shaft 670 is advanced into contact with the receptacle, preventing disengagement of the finger 666 from the receptacle.

Figure 64:
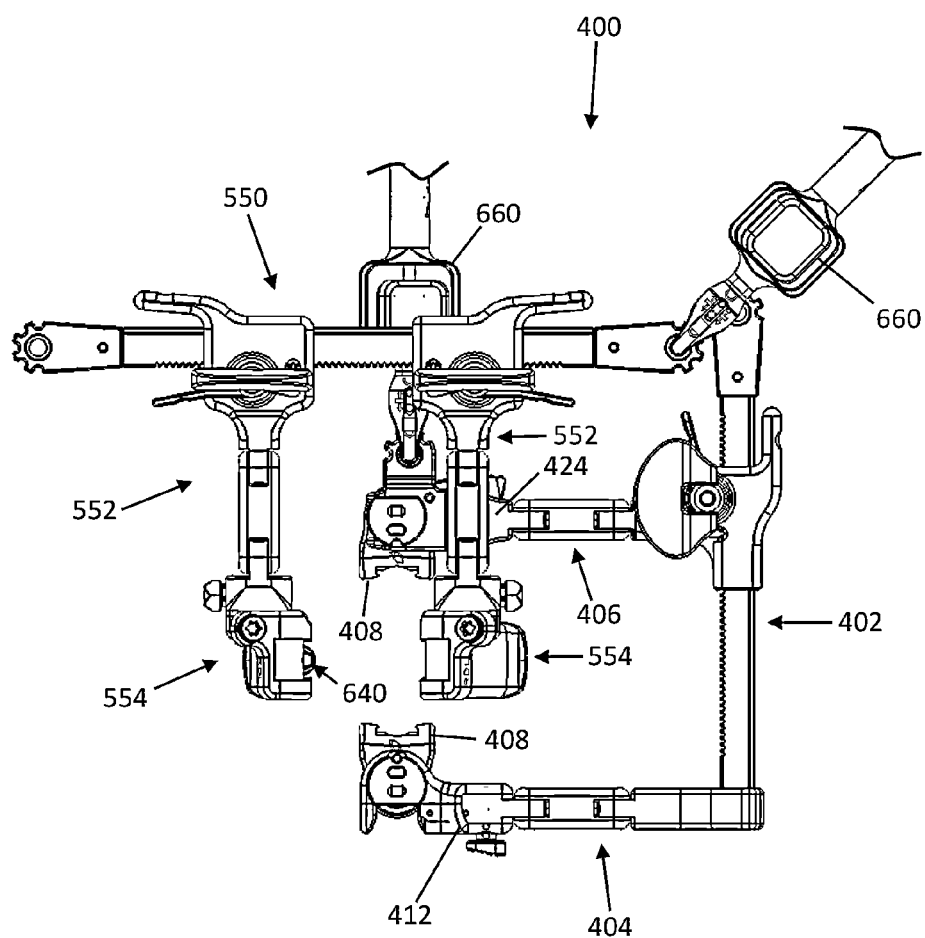
FIG. 64 is a is a top down view of the cervical retractor system of FIG. 29.

According to one example, a method of creating an operative corridor to a cervical target site with the cervical retractor system 400 described with reference to FIG. 64. The medial-lateral retractor 402 is positioned first. The method is initiated by attaching the side loading blade 408 to the insertion instrument 530. The side loading blade 408 is then retracted into the desired position with the insertion instrument. The second side loading blade 408 is then connected to an insertion instrument 530 and retracted into a desired position with the insertion instrument. The straight-on connector 424 and inside-out connector 412 are then attached to the connection post 482 of the respective blades 408. The articulating arm connectors 660 can then be attached to one of the receptors 432 (either on the track 418 to immobilize the base arm 404 or on the straight-on connector 424 to immobilize the moving arm 406). To do so finger 666 of the articulating arm connector 660 is inserted into the receptor with the connector oriented at the desired angle relative to the receptor, and the locking shaft 670 is advanced with the knob 672. A light, for example, a fiber optic light cable configured to mate with the shim track 494, may then be inserted into the shim tracks of the blades 408 to light the operative corridor. The retractor 402 may then be operated to retract tissue in the medial-lateral direction. With the operative corridor established between the blades 408, the cranial-caudal retractor 550 is advanced into position. The blades 554 are first coupled to the blade connectors 564 by sliding the aperture 634 of the connection ledge 618 onto the post 584 until the locking tooth 614 catches the groove within the aperture 634. The distal ends 626 of the blades 554 are advanced through the operative corridor formed by the first retractor 402. A second articulating arm 242 is then attached to one of the receptors 560 on the track 556 to fix the position of the track 556. One or both of the moving arms 554 may then be operated to move the blades 554 away from each other until the exterior faces 622 of the blades engage the soft tissue surrounding the operative corridor. The moving arms may continue to be opened until the distal ends 626 of the blades rest over the cranial most and caudal most vertebral bodies of the exposure. Angulation screws 638 may also be engaged to move the distal ends 626 apart, spreading the distal end of the operative corridor without further expanding the skin incision site. Optionally, distraction shims 640 are slid down the shim tracks 624 and the anchors 644 are anchored into the cranial most and caudal most vertebral bodies. The moving arms 552 can then be separated (and/or the blades can be angulated) to distract the space between the cranial and caudal vertebrae. With the operative corridor established, the surgeon can perform the desired procedure (e.g. discectomy, fusion, disc replacement, etc . . . ).

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. An anterior cervical refractor for application to an anterior part of cervical spine, comprising:
    a medial-lateral retractor, said medial-lateral refractor comprising:
        a base arm and a first retractor blade, the base arm having a first track and a first blade connector, said first track extending perpendicularly from a proximal end of said base arm, said first track including teeth, wherein said first retractor blade couples to the first blade connector such that the first retractor blade can rotate about a limited range relative to the base arm; and
        a first moving arm and a second retractor blade, said first moving arm including a first track receptacle and a second blade connector, said first track receptacle configured to receive said first track extending from said base arm, said first moving arm being translatable along said first track to increase the distance between the moving arm and base arm and retract tissue in medial and lateral directions with the first and second blades, wherein said second retractor blade couples to the second blade connector such that the second retractor blade can rotate about a limited range relative to the moving arm; and
    a cranial-caudal retractor, said cranial-caudal refractor comprising:
        a second track having a plurality of teeth;
        a second moving arm and a third retractor blade, said second moving arm including a second track receptacle and a third blade connector, said second track receptacle configured to receive said second track, wherein said third retractor blade couples to the third blade connector such that the angle of the third retractor blade relative to the third blade connector can be adjusted; and
        a third moving arm and a fourth retractor blade, said third moving arm including a third track receptacle and a fourth blade connector, said third track receptacle configured to receive said second track, wherein said fourth retractor blade couples to the fourth blade connector such that the angle of the fourth retractor blade relative to the fourth blade connector can be adjusted, wherein each of the third moving arm and fourth moving arm are independently translatable along the second track to increase the distance between the second and third moving arms and retract tissue in cranial and caudal directions with the third and fourth retractor blades;
    wherein the first and second blade connectors are side loading connectors, the first blade connector being an inside-out side loading connector, the second blade connector being a straight-on side loading connector, and wherein a connection post on each of the first and second retractor blades is configured to couple with both the inside-out side loading connector and the straight-on side loading connector, the connection post including a lower post rigidly coupled to a blade potion and an upper post coupled to the lower post with limited rotational capability relative to the lower post.

2. The anterior cervical retractor of claim 1, wherein the first retractor blade and the second retractor blade are identical.

3. The anterior cervical retractor of claim 1, wherein each of the first and second retractor blades includes a suction channel designed to receive and maintain a suction instrument within said retractor.

4. The anterior cervical retractor of claim 1, wherein each of the first and second retractor blades includes a light track that receives a lighting element along at least a portion of an interior face thereof.

5. The anterior cervical retractor of claim 1, wherein the first and second retractor blades each include a connection post configured to couple to two instruments simultaneously.

6. The anterior cervical retractor of claim 5, wherein the two instruments comprise two of an insertion instrument, an articulating arm connector, and the retractor.

7. The anterior cervical retractor of claim 1, wherein the third retractor blade and fourth retractor blade are configured to be anchored to the spine.

8. The anterior cervical retractor of claim 7, wherein the third retractor blade and fourth retractor blade each include a shim track configured to receive a distraction shim.

9. The anterior cervical retractor of claim 8, wherein the distraction shim includes a shim and an anchor releaseably associated with the shim.

10. An anterior cervical refractor for application to an anterior part of cervical spine, comprising:
    a medial-lateral retractor, said medial-lateral retractor comprising:
        a base arm and a first retractor blade, the base arm having a first track and a first blade connector, said first track extending perpendicularly from a proximal end of said base arm, said first track including teeth, wherein said first retractor blade couples to the first blade connector such that the first retractor blade can rotate about a limited range relative to the base arm, and the first blade connector is connected to the base arm by a first pivot piece, the first pivot piece including a pair of first pivots, with one pivot located on each end of the first pivot piece to permit adjustment of the height of the first blade connector relative to said base arm while maintaining the alignment of said first blade connector parallel to said base arm, said first pivot piece further including a first friction mechanism for preventing said first blade connector and said first pivot piece from flopping around, said first friction mechanism including a first spring with a pair of first friction nubs situated at each end, said first friction mechanism provided to create friction between said first pivot piece and said first blade connector; and
        a first moving arm and a second retractor blade, said first moving arm including a first track receptacle and a second blade connector, said first track receptacle configured to receive said first track extending from said base arm, said first moving arm being translatable along said first track to increase the distance between the moving arm and base arm and retract tissue in medial and lateral directions with the first and second blades, wherein said second retractor blade couples to the second blade connector such that the second retractor blade can rotate about a limited range relative to the moving arm; and a cranial-caudal retractor, said cranial-caudal refractor comprising:

a second track having a plurality of teeth;

a second moving arm and a third retractor blade, said second moving arm including a second track receptacle and a third blade connector, said second track receptacle configured to receive said second track, wherein said third retractor blade couples to the third blade connector such that the angle of the third retractor blade relative to the third blade connector can be adjusted; and a third moving arm and a fourth retractor blade, said third moving arm including a third track receptacle and a fourth blade connector, said third track receptacle configured to receive said second track, wherein said fourth retractor blade couples to the fourth blade connector such that the angle of the fourth retractor blade relative to the fourth blade connector can be adjusted, wherein each of the third moving arm and fourth moving arm are independently translatable along the second track to increase the distance between the second and third moving arms and retract tissue in a cranial and caudal directions with the third and fourth retractor blades.

11. The anterior cervical retractor of claim 10, wherein the second blade connector is connected to the first moving arm by a second pivot piece, the second pivot piece including a pair of second pivots, with one pivot located on each end of the second pivot piece to permit adjustment of the height of the second blade connector relative to the moving arm while maintaining alignment of the second blade connector parallel to said moving arm, the second pivot piece further including a second friction mechanism for preventing the second blade connector and the second pivot piece from flopping around.

12. The anterior cervical retractor of claim 11, wherein the second friction mechanism includes a second spring having a pair of second friction nubs situated at each end, the second friction mechanism is provided to create friction between the second pivot piece and the second blade connector.

13. The anterior cervical retractor of claim 10, wherein at least one of the first and second retractor blades includes a suction channel designed to receive and maintain a suction instrument within said retractor.

14. The anterior cervical retractor of claim 10, wherein at least one of the first and second retractor blades includes a light track that receives a lighting element along at least a portion of an interior face thereof.

15. The anterior cervical retractor of claim 10, wherein the first retractor blade and second retractor blade each include a connection post configured to couple to two instruments simultaneously.

16. The anterior cervical retractor of claim 15, wherein the two instruments comprise two of an insertion instrument, an articulating arm connector, and the retractor.

17. The anterior cervical retractor of claim 10, wherein the third retractor blade and fourth retractor blade are configured to be anchored to the spine.

18. The anterior cervical retractor of claim 17, wherein the third retractor blade and fourth retractor blade each include a shim track configured to receive a distraction shim.

19. The anterior cervical retractor of claim 18, wherein the distraction shim includes a shim and an anchor releaseably associated with the shim.

* * * * *